US006518029B1

(12) United States Patent
Bandman et al.

(10) Patent No.: US 6,518,029 B1
(45) Date of Patent: Feb. 11, 2003

(54) HUMAN HYDROLASE-LIKE MOLECULES

(75) Inventors: Olga Bandman, Mountain View, CA (US); Preeti Lal, Santa Clara, CA (US); Jennifer L. Hillman, Mountain View, CA (US); Neil C. Corley, Mountain View, CA (US); Karl J. Guegler, Menlo Park, CA (US); Purvi Shah, Sunnyvale, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/612,473

(22) Filed: Jul. 7, 2000

Related U.S. Application Data

(63) Continuation-in-part of application No. 09/013,881, filed on Feb. 6, 1998, now Pat. No. 6,132,964.

(51) Int. Cl.[7] .......................... C12N 9/14; A61K 38/46; G01N 33/53; G01N 33/573
(52) U.S. Cl. .................. 435/7.1; 435/7.21; 435/7.4; 435/183; 435/193; 435/194; 435/195; 435/196; 536/350
(58) Field of Search .................. 530/350; 435/183, 435/195, 196, 193, 194, 7.1, 7.4, 7.21

(56) References Cited

U.S. PATENT DOCUMENTS 5,801,031 A * 9/1998 Galivan et al. .......... 435/172.3

OTHER PUBLICATIONS

Hofman. NCBI Database. National Library of Medicine, National Institutes of Health (Bethesda, MD, USA) Accession No. CAA69330, Sep. 1996.*
Hofman. STREMBL Database. Accession No. P70158, Sep. 1996.*
Ishibashi, T. et al., "Expression cloning of a human dual-specificity phosphatase", *Proc. Natl. Acad. Sci. USA*, 89(24): 12170–12174 (1992).
Krebs, E.G., "Phosphorylation and Dephosphorylation of Glycogen Phosphorlyase: A Prototype for Reversible Covalent Enzyme Modification", *Curr. Top. Cell Regul.*, 18: 401–419 (1981).
Kolch, W. et al., "Protein kinase C activates RAF–1 by direct phosphorylation", *Nature*, 364(6434): 249–252 (1993).
Li, M. et al., "Purification and Characterization of Two Potent Heat–Stable Protein Inhibitors of Protein Phosphatase 2A from Bovine Kidney", *Biochemistry*, 34: 1988–1996 (1995).

Selle, H. et al., "Glycerophosphocholine release in human erythrocytes 1H spin–echo and $^{31}$P–NMR evidence for lysophospholipase", *Eur. J. Biochem.*, 212: 411–416 (1993).
Thornalley, P.J., "Modification of the glyoxalase system in disease processes and prospects for therapeutic strategies", *Biochemical Society Transactions*, 21: 531–534 (1993).
Thornalley, P.J., "The Glyoxalase System in Health and Disease", *Molec. Aspects Med.*, 14: 287–371 (1993).
Frearson, J.A. and D.R. Alexander, "The role of phosphotyrosine phosphatases in haematopoietic cell signal transduction", *BioEssays*, 19: 417–427 (1997).
Goldstein, B.J., "Protein–Tyrosine Phosphatases and the Regulation of Insulin Action", *J. Cell. Biochem.*, 48: 33–42 (1992).
Wilson, R. et al., (Direct Submission) NCBI Accession No. AAB52259 (GI 1938421), Apr. 16, 1997.
Wilson, R. et al., (Direct Submission) NCBI Accession No. U97001 (GI 1938418), Apr. 16, 1997.
Kawasaki, K. et al., (Direct Submission) NCBI Accession No. BAA19990 (GI 2114221), Apr. 14, 2000.
Kawasaki, K. et al., (Direct Submission) NCBI Accession No. D86995 (GI 2114220; GI 2114221), Apr. 14, 2000.
Guan, K. et al., (Direct Submission) NCBI Accession No. AAA34874 (GI 172168), Apr. 27, 1993.
Guan, K. et al., (Direct Submission) NCBI Accession No. L04673 (GI 172167; GI 172168), Apr. 27, 1993.
Ishibashi, T. et al., (Direct Submission) NCBI Accession No. AAA35777 (GI 181840), Apr. 27, 1993.
Ishibashi, T. et al., (Direct Submission) NCBI Accession No. L05147 (GI 181839; GI 181840), Apr. 27, 1993.
Hofmann, K., (Direct Submission) NCBI Accession No. CAA69329 (GI 1552350), Sep. 19, 1996.
Hofmann, K., (Direct Submission) NCBI Accession No. Y08135 (GI 1552349); GI 1552350), Sep. 19, 1996.
Wang, A. et al., (Direct Submission) NCBI Accession No. AAB48627 (GI 1864159), Mar. 5, 1997.
Wang, A. et al., (Direct Submission) NCBI Accession No. U89352 (GI 1864158; GI 1864159), Mar. 5, 1997.
Wintz, H. and W. Sakamoto, (Direct Submission) NCBI Accession No. AAB17995 (GI 1644427), Nov. 1, 1996.
Newman, T. et al., (Direct Submission) NCBI Accession No. U74610 (GI 1644426; GI 1644427), Nov. 2, 1996.

* cited by examiner

*Primary Examiner*—Carla J. Myers
(74) *Attorney, Agent, or Firm*—Incyte Genomics, Inc.

(57) ABSTRACT

The invention provides human hydrolase-like molecules (HHLM) and polynucleotides which identify and encode HHLM. The invention also provides expression vectors, host cells, antibodies, agonists, and antagonists. The invention also provides methods for treating or preventing disorders associated with expression of HHLM.

14 Claims, 3 Drawing Sheets

SEQUENCE LISTING

```
<160> NUMBER OF SEQ ID NOS: 55

<210> SEQ ID NO 1
<211> LENGTH: 259
<212> TYPE: PRT
<213> ORGANISM: Homo sapiens
<220> FEATURE:
<221> NAME/KEY: misc_feature
<223> OTHER INFORMATION: Incyte ID No: 094168

<400> SEQUENCE: 1

Met Ala Ala Cys Arg Ala Leu Lys Ala Val Leu Val Asp Leu Ser
 1               5                  10                  15

Gly Thr Leu His Ile Glu Asp Ala Ala Val Pro Gly Ala Gln Glu
                20                  25                  30

Ala Leu Lys Arg Leu Arg Gly Ala Ser Val Ile Ile Arg Phe Val
                35                  40                  45

Thr Asn Thr Thr Lys Glu Ser Lys Gln Asp Leu Leu Glu Arg Leu
                50                  55                  60

Arg Lys Leu Glu Phe Asp Ile Ser Glu Asp Glu Ile Phe Thr Ser
                65                  70                  75

Leu Thr Ala Ala Arg Ser Leu Leu Glu Arg Lys Gln Val Arg Pro
                80                  85                  90

Met Leu Leu Val Asp Asp Arg Ala Leu Pro Asp Phe Lys Gly Ile
                95                  100                 105

Gln Thr Ser Asp Pro Asn Ala Val Val Met Gly Leu Ala Pro Glu
                110                 115                 120

His Phe His Tyr Gln Ile Leu Asn Gln Ala Phe Arg Leu Leu Leu
                125                 130                 135

Asp Gly Ala Pro Leu Ile Ala Ile His Lys Ala Arg Tyr Tyr Lys
```

-continued

```
                140                 145                 150
Arg Lys Asp Gly Leu Ala Leu Gly Pro Gly Pro Phe Val Thr Ala
                155                 160                 165
Leu Glu Tyr Ala Thr Asp Thr Lys Ala Thr Val Val Gly Lys Pro
                170                 175                 180
Glu Lys Thr Phe Phe Leu Glu Ala Leu Arg Gly Thr Gly Cys Glu
                185                 190                 195
Pro Glu Glu Ala Val Met Ile Gly Asp Cys Arg Asp Asp Val
                200                 205                 210
Gly Gly Ala Gln Asp Val Gly Met Leu Gly Ile Leu Val Lys Thr
                215                 220                 225
Gly Lys Tyr Arg Ala Ser Asp Glu Glu Lys Ile Asn Pro Pro
                230                 235                 240
Tyr Leu Thr Cys Glu Ser Phe Pro His Ala Val Asp His Ile Leu
                245                 250                 255
Gln His Leu Leu

<210> SEQ ID NO 2
<211> LENGTH: 392
<212> TYPE: PRT
<213> ORGANISM: Homo sapiens
<220> FEATURE:
<221> NAME/KEY: misc_feature
<223> OTHER INFORMATION: Incyte ID No: 195647

<400> SEQUENCE: 2

Met Asp Leu Phe Gly Asp Leu Pro Glu Pro Glu Arg Ser Pro Arg
  1               5                  10                  15
Pro Ala Ala Gly Lys Glu Ala Gln Lys Gly Pro Leu Leu Phe Asp
                 20                  25                  30
Asp Leu Pro Pro Ala Ser Ser Thr Asp Ser Gly Ser Gly Gly Pro
                 35                  40                  45
Leu Leu Phe Asp Asp Leu Pro Pro Ala Ser Ser Gly Asp Ser Gly
                 50                  55                  60
Ser Leu Ala Thr Ser Ile Ser Gln Met Val Lys Thr Glu Gly Lys
                 65                  70                  75
Gly Ala Lys Arg Lys Thr Ser Glu Glu Glu Lys Asn Gly Ser Glu
                 80                  85                  90
Glu Leu Val Glu Lys Lys Val Cys Lys Ala Ser Ser Val Ile Phe
                 95                 100                 105
Gly Leu Lys Gly Tyr Val Ala Glu Arg Lys Gly Glu Arg Glu Glu
                110                 115                 120
Met Gln Asp Ala His Val Ile Leu Asn Asp Ile Thr Glu Glu Cys
                125                 130                 135
Arg Pro Pro Ser Ser Leu Ile Thr Arg Val Ser Tyr Phe Ala Val
                140                 145                 150
Phe Asp Gly His Gly Gly Ile Arg Ala Ser Lys Phe Ala Ala Gln
                155                 160                 165
Asn Leu His Gln Asn Leu Ile Arg Lys Phe Pro Lys Gly Asp Val
                170                 175                 180
Ile Ser Val Glu Lys Thr Val Lys Arg Cys Leu Leu Asp Thr Phe
                185                 190                 195
Lys His Thr Asp Glu Glu Phe Leu Lys Gln Ala Ser Ser Gln Lys
                200                 205                 210
Pro Ala Trp Lys Asp Gly Ser Thr Ala Thr Cys Val Leu Ala Val
```

```
                215                 220                 225

Asp Asn Ile Leu Tyr Ile Ala Asn Leu Gly Asp Ser Arg Ala Ile
                230                 235                 240

Leu Cys Arg Tyr Asn Glu Glu Ser Gln Lys His Ala Ala Leu Ser
                245                 250                 255

Leu Ser Lys Glu His Asn Pro Thr Gln Tyr Glu Glu Arg Met Arg
                260                 265                 270

Ile Gln Lys Ala Gly Gly Asn Val Arg Asp Gly Arg Val Leu Gly
                275                 280                 285

Val Leu Glu Val Ser Arg Ser Ile Gly Asp Gly Gln Tyr Lys Arg
                290                 295                 300

Cys Gly Val Thr Ser Val Pro Asp Ile Arg Arg Cys Gln Leu Thr
                305                 310                 315

Pro Asn Asp Arg Phe Ile Leu Leu Ala Cys Asp Gly Leu Phe Lys
                320                 325                 330

Val Phe Thr Pro Glu Glu Ala Val Asn Phe Ile Leu Ser Cys Leu
                335                 340                 345

Glu Asp Glu Lys Ile Gln Thr Arg Glu Gly Lys Ser Ala Ala Asp
                350                 355                 360

Ala Arg Tyr Glu Ala Ala Cys Asn Arg Leu Ala Asn Lys Ala Val
                365                 370                 375

Gln Arg Gly Ser Ala Asp Asn Val Thr Val Met Val Val Arg Ile
                380                 385                 390

Gly His

<210> SEQ ID NO 3
<211> LENGTH: 353
<212> TYPE: PRT
<213> ORGANISM: Homo sapiens
<220> FEATURE:
<221> NAME/KEY: misc_feature
<223> OTHER INFORMATION: Incyte ID No: 507537

<400> SEQUENCE: 3

Met Val Gly Gln Glu Ala Ala Leu Ser Leu Gly Ala Ala Met Leu
  1               5                  10                  15

Glu Ala Pro Gly Pro Ser Asp Gly Cys Glu Leu Ser Asn Pro Ser
                 20                  25                  30

Ala Ser Arg Val Ser Cys Ala Gly Gln Met Leu Glu Val Gln Pro
                 35                  40                  45

Gly Leu Tyr Phe Gly Gly Ala Ala Val Ala Glu Pro Asp His
                 50                  55                  60

Leu Arg Glu Ala Gly Ile Thr Ala Val Leu Thr Val Asp Ser Glu
                 65                  70                  75

Glu Pro Ser Phe Lys Ala Gly Pro Gly Val Glu Asp Leu Trp Arg
                 80                  85                  90

Leu Phe Val Pro Ala Leu Asp Lys Pro Glu Thr Asp Leu Leu Ser
                 95                 100                 105

His Leu Asp Arg Cys Val Ala Phe Ile Gly Gln Ala Arg Ala Glu
                110                 115                 120

Gly Arg Ala Val Leu Val His Cys His Ala Gly Val Ser Arg Ser
                125                 130                 135

Val Ala Ile Ile Thr Ala Phe Leu Met Lys Thr Asp Gln Leu Pro
                140                 145                 150

Phe Glu Lys Ala Tyr Glu Lys Leu Gln Ile Leu Lys Pro Glu Ala
```

-continued

```
            155                 160                 165

Lys Met Asn Glu Gly Phe Glu Trp Gln Leu Lys Leu Tyr Gln Ala
            170                 175                 180

Met Gly Tyr Glu Val Asp Thr Ser Ser Ala Ile Tyr Lys Gln Tyr
            185                 190                 195

Arg Leu Gln Lys Val Thr Glu Lys Tyr Pro Glu Leu Gln Asn Leu
            200                 205                 210

Pro Gln Glu Leu Phe Ala Val Asp Pro Thr Thr Val Ser Gln Gly
            215                 220                 225

Leu Lys Asp Glu Val Leu Tyr Lys Cys Arg Lys Cys Arg Arg Ser
            230                 235                 240

Leu Phe Arg Ser Ser Ile Leu Asp His Arg Glu Gly Ser Gly
            245                 250                 255

Pro Ile Ala Phe Ala His Lys Arg Met Thr Pro Ser Ser Met Leu
            260                 265                 270

Thr Thr Gly Arg Gln Ala Gln Cys Thr Ser Tyr Phe Ile Glu Pro
            275                 280                 285

Val Gln Trp Met Glu Ser Ala Leu Leu Gly Val Met Asp Gly Gln
            290                 295                 300

Leu Leu Cys Pro Lys Cys Ser Ala Lys Leu Gly Ser Phe Asn Trp
            305                 310                 315

Tyr Gly Glu Gln Cys Ser Cys Gly Arg Trp Ile Thr Pro Ala Phe
            320                 325                 330

Gln Ile His Lys Asn Arg Val Asp Glu Met Lys Ile Leu Pro Val
            335                 340                 345

Leu Gly Ser Gln Thr Gly Lys Ile
            350

<210> SEQ ID NO 4
<211> LENGTH: 207
<212> TYPE: PRT
<213> ORGANISM: Homo sapiens
<220> FEATURE:
<221> NAME/KEY: misc_feature
<223> OTHER INFORMATION: Incyte ID No: 971204

<400> SEQUENCE: 4

Met Cys Pro Gly Asn Trp Leu Trp Ala Ser Met Thr Phe Met Ala
 1               5                  10                  15

Arg Phe Ser Arg Ser Ser Arg Ser Pro Val Arg Thr Arg Gly
            20                  25                  30

Thr Leu Glu Glu Met Pro Thr Val Gln His Pro Phe Leu Asn Val
            35                  40                  45

Phe Glu Leu Glu Arg Leu Leu Tyr Thr Gly Lys Thr Ala Cys Asn
            50                  55                  60

His Ala Asp Glu Val Trp Pro Gly Leu Tyr Leu Gly Asp Gln Asp
            65                  70                  75

Met Ala Asn Asn Arg Arg Glu Leu Arg Arg Leu Gly Ile Thr His
            80                  85                  90

Val Leu Asn Ala Ser His Ser Arg Trp Arg Gly Thr Pro Glu Ala
            95                 100                 105

Tyr Glu Gly Leu Gly Ile Arg Tyr Leu Gly Val Glu Pro Ala Phe
            110                 115                 120

Asp Met Ser Ile His Phe Gln Thr Ala Ala Asp Phe Ile His Arg
            125                 130                 135
```

-continued

```
Ala Leu Ser Gln Pro Gly Gly Lys Ile Leu Val His Cys Ala Val
            140                 145                 150

Gly Val Ser Arg Ser Ala Thr Leu Val Leu Ala Tyr Leu Met Leu
            155                 160                 165

Tyr His His Leu Thr Leu Val Glu Ala Ile Lys Lys Val Lys Asp
            170                 175                 180

His Arg Gly Ile Ile Pro Asn Arg Gly Phe Leu Arg Gln Leu Leu
            185                 190                 195

Ala Leu Asp Arg Arg Leu Arg Gln Gly Leu Glu Ala
            200                 205
```

<210> SEQ ID NO 5
<211> LENGTH: 453
<212> TYPE: PRT
<213> ORGANISM: Homo sapiens
<220> FEATURE:
<221> NAME/KEY: misc_feature
<223> OTHER INFORMATION: Incyte ID No: 1376382

<400> SEQUENCE: 5

```
Met Ala Leu Val Arg Ala Leu Val Cys Cys Leu Leu Thr Ala Trp
 1               5                  10                  15

His Cys Arg Ser Gly Leu Gly Leu Pro Val Ala Pro Ala Gly Gly
            20                  25                  30

Arg Asn Pro Pro Pro Ala Ile Gly Gln Phe Trp His Val Thr Asp
            35                  40                  45

Leu His Leu Asp Pro Thr Tyr His Ile Thr Asp Asp His Thr Lys
            50                  55                  60

Val Cys Ala Ser Ser Lys Gly Ala Asn Ala Ser Asn Pro Gly Pro
            65                  70                  75

Phe Gly Asp Val Leu Cys Asp Ser Pro Tyr Gln Leu Ile Leu Ser
            80                  85                  90

Ala Phe Asp Phe Ile Lys Asn Ser Gly Gln Glu Ala Ser Phe Met
            95                  100                 105

Ile Trp Thr Gly Asp Ser Pro His Val Pro Val Pro Glu Leu
            110                 115                 120

Ser Thr Asp Thr Val Ile Asn Val Ile Thr Asn Met Thr Thr Thr
            125                 130                 135

Ile Gln Ser Leu Phe Pro Asn Leu Gln Val Phe Pro Ala Leu Gly
            140                 145                 150

Asn His Asp Tyr Trp Pro Gln Asp Gln Leu Pro Val Val Thr Ser
            155                 160                 165

Lys Val Tyr Asn Ala Val Ala Asn Leu Trp Lys Pro Trp Leu Asp
            170                 175                 180

Glu Glu Ala Ile Ser Thr Leu Arg Lys Gly Gly Phe Tyr Ser Gln
            185                 190                 195

Lys Val Thr Thr Asn Pro Asn Leu Arg Ile Ile Ser Leu Asn Thr
            200                 205                 210

Asn Leu Tyr Tyr Gly Pro Asn Ile Met Thr Leu Asn Lys Thr Asp
            215                 220                 225

Pro Ala Asn Gln Phe Glu Trp Leu Glu Ser Thr Leu Asn Asn Ser
            230                 235                 240

Gln Gln Asn Lys Glu Lys Val Tyr Ile Ile Ala His Val Pro Val
            245                 250                 255

Gly Tyr Leu Pro Ser Ser Gln Asn Ile Thr Ala Met Arg Glu Tyr
            260                 265                 270
```

-continued

```
Tyr Asn Glu Lys Leu Ile Asp Ile Phe Gln Lys Tyr Ser Asp Val
                275                 280                 285

Ile Ala Gly Gln Phe Tyr Gly His Thr His Arg Asp Ser Ile Met
                290                 295                 300

Val Leu Ser Asp Lys Lys Gly Ser Pro Val Asn Ser Leu Phe Val
                305                 310                 315

Ala Pro Ala Val Thr Pro Val Lys Ser Val Leu Glu Lys Gln Thr
                320                 325                 330

Asn Asn Pro Gly Ile Arg Leu Phe Gln Tyr Asp Pro Arg Asp Tyr
                335                 340                 345

Lys Leu Leu Asp Met Leu Gln Tyr Tyr Leu Asn Leu Thr Glu Ala
                350                 355                 360

Asn Leu Lys Gly Glu Ser Ile Trp Lys Leu Glu Tyr Ile Leu Thr
                365                 370                 375

Gln Thr Tyr Asp Ile Glu Asp Leu Gln Pro Glu Ser Leu Tyr Gly
                380                 385                 390

Leu Ala Lys Gln Phe Thr Ile Leu Asp Ser Lys Gln Phe Ile Lys
                395                 400                 405

Tyr Tyr Asn Tyr Phe Phe Val Ser Tyr Asp Ser Ser Val Thr Cys
                410                 415                 420

Asp Lys Thr Cys Lys Ala Phe Gln Ile Cys Ala Ile Met Asn Leu
                425                 430                 435

Asp Asn Ile Ser Tyr Ala Asp Cys Leu Lys Gln Leu Tyr Ile Lys
                440                 445                 450

His Asn Tyr

<210> SEQ ID NO 6
<211> LENGTH: 270
<212> TYPE: PRT
<213> ORGANISM: Homo sapiens
<220> FEATURE:
<221> NAME/KEY: misc_feature
<223> OTHER INFORMATION: Incyte ID No: 2011230

<400> SEQUENCE: 6

Met Ala Pro Trp Gly Lys Arg Leu Ala Gly Val Arg Gly Val Leu
  1               5                  10                  15

Leu Asp Ile Ser Gly Val Leu Tyr Asp Ser Gly Ala Gly Gly Gly
                 20                  25                  30

Thr Ala Ile Ala Gly Ser Val Glu Ala Val Ala Arg Leu Lys Arg
                 35                  40                  45

Ser Arg Leu Lys Val Arg Phe Cys Thr Asn Glu Ser Gln Lys Ser
                 50                  55                  60

Arg Ala Glu Leu Val Gly Gln Leu Gln Arg Leu Gly Phe Asp Ile
                 65                  70                  75

Ser Glu Gln Glu Val Thr Ala Pro Ala Pro Ala Ala Cys Gln Ile
                 80                  85                  90

Leu Lys Glu Gln Gly Leu Arg Pro Tyr Leu Leu Ile His Asp Gly
                 95                 100                 105

Val Arg Ser Glu Phe Asp Gln Ile Asp Thr Ser Asn Pro Asn Cys
                110                 115                 120

Val Val Ile Ala Asp Ala Gly Glu Ser Phe Ser Tyr Gln Asn Met
                125                 130                 135

Asn Asn Ala Phe Gln Val Leu Met Glu Leu Glu Lys Pro Val Leu
                140                 145                 150
```

```
Ile Ser Leu Gly Lys Gly Arg Tyr Tyr Lys Glu Thr Ser Gly Leu
            155                 160                 165

Met Leu Asp Val Gly Pro Tyr Met Lys Ala Leu Glu Tyr Ala Cys
            170                 175                 180

Gly Ile Lys Ala Glu Val Gly Lys Pro Ser Pro Glu Phe Phe
            185                 190                 195

Lys Ser Ala Leu Gln Ala Ile Gly Val Glu Ala His Gln Ala Val
            200                 205                 210

Met Ile Gly Asp Asp Ile Val Gly Asp Val Gly Gly Ala Gln Arg
            215                 220                 225

Cys Gly Met Arg Ala Leu Gln Val Arg Thr Gly Lys Phe Arg Pro
            230                 235                 240

Ser Asp Glu His His Pro Glu Val Lys Ala Asp Gly Tyr Val Asp
            245                 250                 255

Asn Leu Ala Glu Ala Val Asp Leu Leu Leu Gln His Ala Asp Lys
            260                 265                 270

<210> SEQ ID NO 7
<211> LENGTH: 231
<212> TYPE: PRT
<213> ORGANISM: Homo sapiens
<220> FEATURE:
<221> NAME/KEY: misc_feature
<223> OTHER INFORMATION: Incyte ID No: 2768301

<400> SEQUENCE: 7

Met Cys Gly Asn Thr Met Ser Val Pro Leu Leu Thr Asp Ala Ala
  1               5                  10                  15

Thr Val Ser Gly Ala Glu Arg Glu Thr Ala Ala Val Ile Phe Leu
             20                  25                  30

His Gly Leu Gly Asp Thr Gly His Ser Trp Ala Asp Ala Leu Ser
             35                  40                  45

Thr Ile Arg Leu Pro His Val Lys Tyr Ile Cys Pro His Ala Pro
             50                  55                  60

Arg Ile Pro Val Thr Leu Asn Met Lys Met Val Met Pro Ser Trp
             65                  70                  75

Phe Asp Leu Met Gly Leu Ser Pro Asp Ala Pro Glu Asp Glu Ala
             80                  85                  90

Gly Ile Lys Lys Ala Ala Glu Asn Ile Lys Ala Leu Ile Glu His
             95                 100                 105

Glu Met Lys Asn Gly Ile Pro Ala Asn Arg Ile Val Leu Gly Gly
            110                 115                 120

Phe Ser Gln Gly Gly Ala Leu Ser Leu Tyr Thr Ala Leu Thr Cys
            125                 130                 135

Pro His Pro Leu Ala Gly Ile Val Ala Leu Ser Cys Trp Leu Pro
            140                 145                 150

Leu His Arg Ala Phe Pro Gln Ala Ala Asn Gly Ser Ala Lys Asp
            155                 160                 165

Leu Ala Ile Leu Gln Cys His Gly Glu Leu Asp Pro Met Val Pro
            170                 175                 180

Val Arg Phe Gly Ala Leu Thr Ala Glu Lys Leu Arg Ser Val Val
            185                 190                 195

Thr Pro Ala Arg Val Gln Phe Lys Thr Tyr Pro Gly Val Met His
            200                 205                 210

Ser Ser Cys Pro Gln Glu Met Ala Ala Val Lys Glu Phe Leu Glu
```

```
                    215                 220                 225

Lys Leu Leu Pro Pro Val
                230

<210> SEQ ID NO 8
<211> LENGTH: 254
<212> TYPE: PRT
<213> ORGANISM: Homo sapiens
<220> FEATURE:
<221> NAME/KEY: misc_feature
<223> OTHER INFORMATION: Incyte ID No: 2886583

<400> SEQUENCE: 8

Met Ala Glu Ala Val Leu Arg Val Ala Arg Arg Gln Leu Ser Gln
 1               5                  10                  15

Arg Gly Gly Ser Gly Ala Pro Ile Leu Arg Gln Met Phe Glu
                20                  25                  30

Pro Val Ser Cys Thr Phe Thr Tyr Leu Leu Gly Asp Arg Glu Ser
                35                  40                  45

Arg Glu Ala Val Leu Ile Asp Pro Val Leu Glu Thr Ala Pro Arg
                50                  55                  60

Asp Ala Gln Leu Ile Lys Glu Leu Gly Leu Arg Leu Leu Tyr Ala
                65                  70                  75

Val Asn Thr His Cys His Ala Asp His Ile Thr Gly Ser Gly Leu
                80                  85                  90

Leu Arg Ser Leu Leu Pro Gly Cys Gln Ser Val Ile Ser Arg Leu
                95                 100                 105

Ser Gly Ala Gln Ala Asp Leu His Ile Glu Asp Gly Asp Ser Ile
                110                115                 120

Arg Phe Gly Arg Phe Ala Leu Glu Thr Arg Ala Ser Pro Gly His
                125                130                 135

Thr Pro Gly Cys Val Thr Phe Val Leu Asn Asp His Ser Met Ala
                140                145                 150

Phe Thr Gly Asp Ala Leu Leu Ile Arg Gly Cys Gly Arg Thr Asp
                155                160                 165

Phe Gln Gln Gly Cys Ala Lys Thr Leu Tyr His Ser Val His Glu
                170                175                 180

Lys Ile Phe Thr Leu Pro Gly Asp Cys Leu Ile Tyr Pro Ala His
                185                190                 195

Asp Tyr His Gly Phe Thr Val Ser Thr Val Glu Glu Glu Arg Thr
                200                205                 210

Leu Asn Pro Arg Leu Thr Leu Ser Cys Glu Glu Phe Val Lys Ile
                215                220                 225

Met Gly Asn Leu Asn Leu Pro Lys Pro Gln Gln Ile Asp Phe Ala
                230                235                 240

Val Pro Ala Asn Met Arg Cys Gly Val Gln Thr Pro Thr Ala
                245                250

<210> SEQ ID NO 9
<211> LENGTH: 2162
<212> TYPE: DNA
<213> ORGANISM: Homo sapiens
<220> FEATURE:
<221> NAME/KEY: misc_feature
<223> OTHER INFORMATION: Incyte ID No: 094168

<400> SEQUENCE: 9
gtcgggcagc agcggggctg tctatcccgg ctgaggaccc gcggccagtg cgggtggctg      60
```

```
gctttgccat tagcgggggc ctttcctgag gacggcgtac ggagtgtggg gaatgaagga    120
tggcagcatg ccgtgcatta aaagctgttt tggtagatct cagtggcaca cttcacattg    180
aagatgcagc tgtgccaggc gcacaggaag ctcttaaaag gttacgtggt gcttctgtaa    240
tcattaggtt tgtgaccaat acaaccaaag agagcaagca agacctgtta gaaaggttga    300
gaaaattgga atttgatatc tctgaagatg aaatattcac atctctgact gcagccagaa    360
gtttactaga gcggaaacaa gtcagaccca tgctgctagt tgatgatcgg gcactacctg    420
atttcaaagg aatacaaaca agtgatccta atgctgtggt catgggattg gcaccagaac    480
attttcatta tcaaattctg aatcaagcat tccggttact cctggatgga gcacctctga    540
tagcaatcca caaagccagg tattacaaga ggaaagatgg cttagccctg gggcctggac    600
catttgtgac tgctttagag tatgccacag ataccaaagc cacagtcgtg gggaaaccag    660
agaagacgtt cttttttggaa gcattgcggg gcactggctg tgaacctgag gaggctgtca    720
tgataggaga tgattgcagg gatgatgttg gtggggctca agatgtcggc atgctgggca    780
tcttagtaaa gactgggaaa tatcgagcat cagatgaaga aaaaattaat ccacctcctt    840
acttaacttg tgagagtttc cctcatgctg tggaccacat tctgcagcac ctattgtgaa    900
gcaatgtgtg catctgaagc aacttgaaat gcagcttctt attgtctgga atgaatccct    960
taccaactca gtgccagcat cggtagacac cagtcagtgc tgatcgcttt ttaaccctct   1020
tttgttgtgc attaattaga aagaaaggta ttgaattgcg gctagccagt aagccttgct   1080
aatctctttt attttgtaac tgaagatgag acccaaagaa agggaaagct gagattttgt   1140
gccattcctt ttaaaatatt catcaggtta ggtgggggctg tgggggaaaa gctaccacag   1200
ggaagagtgt tctctgctgt ctcttcactg gaaaacaggg aggggggatt tcagactgtg   1260
aagaaagttg aatggtggtt tttaaattat aaagtaatgt attaaaaggt gcattaggct   1320
gtagttctaa tattgagttc aactgtgaaa tccatcagat gtgccaaatg gagaagacag   1380
aaagcaacaa agtgaattgt tctttagccc aagtggtaca gtgaatttgc tttaacagat   1440
gttgaaaact aaattttcta ctgtattccc agcacgggtg acttcttttt ctcttcatta   1500
gccagagatg actaatttaa atttagaacc agattttaat ttaaattaat atttccatta   1560
ataacctatt cattgcagat acctattata ctgtgtaaca gttgttttgg aaattttatg   1620
taaaattaaa actatcagta ttttacagat gttttaatta gacattgtta ttaacaggaa   1680
cagtgcagaa actagaatca agccttataa tatcttatag accatgcatt tttgaagtta   1740
gtgtccacta gggtcctatt aactgtacat ttgcaagatt tcattatttt tgcctctgac   1800
actatgggaa aaatttttta gaagctattg ggacagattc aagcttttat gcacttggtt   1860
actacagctg taaaatgaaa tctcgtcttg tagcatggat tattcttctc atgttaaacc   1920
caccaaaata aaggggacta aataggtaat gattttccta gtgcatttgc atactgtgat   1980
aatcctgggc cttgcaatag ttctacaggg ctcttgggca ttgaattatt aggatgtaat   2040
tgtacatcat tgtagtgttc accttattga agctcactct gatgttaatg agcttcgggt   2100
tttgatgctt gtttagagat cagcagtctt ggatgggagg gaacaaagct aaataaatgt   2160
ta                                                                 2162

<210> SEQ ID NO 10
<211> LENGTH: 1403
<212> TYPE: DNA
<213> ORGANISM: Homo sapiens
<220> FEATURE:
```

<221> NAME/KEY: misc_feature
<223> OTHER INFORMATION: Incyte ID No: 195647

<400> SEQUENCE: 10

| | | | | | |
|---|---|---|---|---|---|
| cggggtgtgg | agcccggccg | ctgctcgcgg | gctgagtgtc | tgtcgctgct | gccgcctcca | 60 |
| cccagcctcc | gccatggacc | tcttcgggga | cctgccggag | cccgagcgct | cgccgcgccc | 120 |
| ggctgccggg | aaagaagctc | agaaaggacc | cctgctcttt | gatgacctcc | ctccggccag | 180 |
| cagtactgac | tcaggatcag | ggggaccttt | gcttttgat | gatctcccac | ccgctagcag | 240 |
| tggcgattca | ggttctcttg | ccacatcaat | atcccagatg | gtaaagactg | aagggaaagg | 300 |
| agcaaagaga | aaaacctccg | aggaagagaa | gaatggcagt | gaagagcttg | tggaaaagaa | 360 |
| agtttgtaaa | gcctcttcgg | tgatcttttgg | tctgaagggc | tatgtggctg | agcggaaggg | 420 |
| tgagagggag | gagatgcagg | atgcccacgt | catcctgaac | gacatcaccg | aggagtgtag | 480 |
| gcccccatcg | tccctcatta | ctcgggtttc | atattttgct | gttttttgatg | gacatggagg | 540 |
| aattcgagcc | tcaaaatttg | ctgcacagaa | tttgcatcaa | aacttaatca | gaaaatttcc | 600 |
| taaggagat | gtaatcagtg | tagagaaaac | cgtgaagaga | tgccttttgg | acactttcaa | 660 |
| gcatactgat | gaagagttcc | ttaaacaagc | ttccagccag | aagcctgcct | ggaaagatgg | 720 |
| gtccactgcc | acgtgtgttc | tggctgtaga | caacattctt | tatattgcca | acctcggaga | 780 |
| tagtcgggca | atcttgtgtc | gttataatga | ggagagtcaa | aaacatgcag | ccttaagcct | 840 |
| cagcaaagag | cataatccaa | ctcagtatga | agagcggatg | aggatacaga | aggctggagg | 900 |
| aaacgtcagg | gatgggcgtg | ttttgggcgt | gctagaggtg | tcacgctcca | ttggggacgg | 960 |
| gcagtacaag | cgctgcggtg | tcacctctgt | gcccgacatc | agacgctgcc | agctgacccc | 1020 |
| caatgacagg | ttcattttgt | tggcctgtga | tgggctcttc | aaggtcttta | ccccagaaga | 1080 |
| agccgtgaac | ttcatcttgt | cctgtctcga | ggatgaaaag | atccagaccc | gggaagggaa | 1140 |
| gtccgcagcc | gacgcccgct | acgaagcagc | ctgcaacagg | ctggccaaca | aggcggtgca | 1200 |
| gcggggctcg | gccgacaacg | tcactgtgat | ggtggtgcgg | ataggcact | gagggtggc | 1260 |
| gcgcggccag | gagcacgcat | ggtattgact | taaaaggttc | attttgtgtg | tgtgcacatt | 1320 |
| gtgtgttttg | tgtactcctg | tgggactccc | atggttgtaa | ataaaggttt | ctcttttttt | 1380 |
| ttcctaaaaa | aaaaaaaaaa | aaa | | | | 1403 |

<210> SEQ ID NO 11
<211> LENGTH: 1358
<212> TYPE: DNA
<213> ORGANISM: Homo sapiens
<220> FEATURE:
<221> NAME/KEY: misc_feature
<223> OTHER INFORMATION: Incyte ID No: 507537

<400> SEQUENCE: 11

| | | | | | |
|---|---|---|---|---|---|
| gtaccacgcg | tccgagagcc | gccgaggctg | gcgagtccca | ggggaaggat | gttctagccg | 60 |
| gagtctactc | gatggtaggg | caggaagccg | ccttgtctct | gggcgcggcc | atgttggagg | 120 |
| ctccgggccc | gagtgatggc | tgcgagctca | gcaacccag | cgccagcaga | gtcagctgtg | 180 |
| ccgggcagat | gctggaagtg | cagccaggat | tgtatttcgg | tggggccgcg | gccgtcgcgg | 240 |
| agccagatca | cctgagggaa | gcgggcatca | cggccgtgct | aacagtggac | tcggaggagc | 300 |
| ccagcttcaa | ggcggggcct | ggggtcgagg | atctatggcg | cctcttcgtg | ccagcgctgg | 360 |
| acaaacccga | gacggaccta | ctcagccatc | tggaccggtg | cgtggccttc | atcggtcagg | 420 |
| cccgcgctga | gggccgtgcg | gtgttggtgc | actgtcatgc | aggagtcagt | cgaagtgtgg | 480 |

```
ccataataac tgcttttctc atgaagactg accaacttcc ctttgaaaaa gcctatgaaa      540
agctccagat tctcaaacca gaggctaaga tgaatgaggg gtttgagtgg caactgaaat      600
tataccaggc aatgggatac gaagtggata cctctagtgc aatttataag caatatcgtt      660
tacaaaaggt tacagagaag tatccagaat tgcagaattt acctcaagaa ctctttgctg      720
ttgacccaac taccgtttca caaggattga agatgaggg tctctacaag tgtagaaagt       780
gcaggcgatc attatttcga agttctagta ttctggatca ccgtgaagga agtggaccta      840
tagcctttgc ccacaagaga atgacaccat cttccatgct taccacaggg aggcaagctc      900
aatgtacatc ttatttcatt gaacctgtac agtggatgga atctgctttg ttgggagtga      960
tggatggaca gcttctttgc ccaaaatgca gtgccaagtg gggttccttc aactggtatg     1020
gtgaacagtg ctcttgtggt aggtggataa cacctgcttt tcaaatacat aagaatagag     1080
tggatgaaat gaaatatttg cctgttttgg gatcacaaac aggaaaaata tgaacatgat     1140
attttatagc ttgggaagaa acttgcagat gatatgtgct gcctttgctt cttatcattc     1200
atggcagatt gtttgtgctt tcaacatttc atttgaaatg ggagaagata aaatcacttg     1260
atgtaacctg gaaactatgc tttacatggc aatcaaagcc ttttgatcat gtacatttta     1320
tttgatatta aaatcttttta taaccagaaa aaaaaaaa                            1358

<210> SEQ ID NO 12
<211> LENGTH: 1691
<212> TYPE: DNA
<213> ORGANISM: Homo sapiens
<220> FEATURE:
<221> NAME/KEY: misc_feature
<223> OTHER INFORMATION: Incyte ID No: 971204

<400> SEQUENCE: 12
cacgcatgca ttccaggcgg tgctgctggg gctcggcggg gccgtgtctg gtctgcaagg       60
cgcgcgggct cgtgggggt tggctgggga gcccacgctg cctggcgact cgggccaccg      120
aatgtgagac cgagtccctt tatgtcacca gcgcacacgc tgatttgaac cctgcttcga      180
cgtgtgtgtc atggcttaaa aatagctgct aatctgtcaa cctgtcttgg gcagaaacag      240
cggcggcgac agcagcagga gcgtcatggc cgtggcgctg tctgcgccgg cgatccgcct      300
ttcggactga ggcccagcgc agcgcttgca aagagcagca gctacctggc aactgaaccc      360
atcatcacca cagccactcc tgcagctgcc acggtttctg ccacctctaa gatgtgccct      420
ggtaactggc tttgggcttc tatgactttt atggctcgct tctcccggag tagctcaagg      480
tctcctgttc gaactcgagg gaccctggag gagatgccaa ccgttcaaca tcctttcctc      540
aatgtcttcg agttggagcg gctcctctac acaggcaaga cagcctgtaa ccatgccgac      600
gaggtctggc caggcctcta tctcggagac caggacatgg ctaacaaccg ccgggagctt      660
cgccgcctgg gcatcacgca cgtcctcaat gcctcacaca gccggtggcg aggcacgccc      720
gaggcctatg aggggctggg catccgctac ctgggtgttg agccagcctt tgacatgagc      780
atccacttcc agacggctgc cgacttcatc caccgggcgc tgagccagcc aggagggaag      840
atcctggtgc attgtgctgt gggcgtgagc cgatccgcca ccctggtact ggcctacctc      900
atgctgtacc accaccttac cctcgtggag gccatcaaga aagtcaaaga ccaccgaggc      960
atcatcccca accggggctt cctgaggcag ctcctggccc tggaccgcag gctgcggcag     1020
ggtctggaag catgaggggga gggggagaga ggtcaggcca ggcccgtggg taggtccctg     1080
gctcccagct ggagatagga ggcccaggtg gcaggtagca ggaggcccag atcacccatc     1140
```

```
ctcccctggg gtcaggagag gccgagcccc aggccactgt cactctttgc gggaggggac    1200
ggggagtgag gttgggcagt gtggtggatg ggcacccagg aagggttgac cagggaagga    1260
ggcagctagg ctgtagatgg aagatggtcc tgggattcga acaccgctgg gatctggcta    1320
gggtgctccc tgggattcac agtcccttcc cctctttgtg cccaagtgtt tccctctctc    1380
cctcaccaaa acaaaagggc catctctgcc ctgcacttgt gcagaaagtc agggatacgg    1440
caagcatgaa tgcaatggtg tagagttgtg tgaaacccct agcatagaga cagacagcga    1500
agagatggtg tgaaaagctt gcagaaccag acagagaacc ccacgacttt ccactccaa    1560 gcacaggagg aggtagctag cgtgtgaggg ttggcactag gcccacggct gctgcttggg    1620
ccaaaaacat acagaggtgc atggctggca gtcttgaaat tgtcactcgc ttactggatc    1680
caagtgtctc g                                                        1691
```

<210> SEQ ID NO 13
<211> LENGTH: 1764
<212> TYPE: DNA
<213> ORGANISM: Homo sapiens
<220> FEATURE:
<221> NAME/KEY: misc_feature
<223> OTHER INFORMATION: Incyte ID No: 1376382

<400> SEQUENCE: 13

```
ctcaggcctg acgtccgag tggagctgcg ggacagcccg aacctccagg tcagccccgc     60
ggccctccat ggcgctggtg cgcgcactcg tctgctgcct gctgactgcc tggcactgcc    120
gctccggcct cgggctgccc gtggcgcccg caggcggcag gaatcctcct ccggcgatag    180
gacagttttg gcatgtgact gacttacact tagaccctac ttaccacatc acagatgacc    240
acacaaaagt gtgtgcttca tctaaaggtg caaatgcctc caaccctggc ccttttggag    300
atgttctgtg tgattctcca tatcaactta ttttgtcagc atttgatttt attaaaaatt    360
ctggacaaga agcatctttc atgatatgga caggggatag cccacctcat gttcctgtac    420
ctgaactctc aacagacact gttataaatg tgatcactaa tatgacaacc accatccaga    480
gtctctttcc aaatctccag gttttccctg cgctgggtaa tcatgactat tggccacagg    540
atcaactgcc tgtagtcacc agtaaagtgt acaatgcagt agcaaacctc tggaaaccat    600
ggctagatga agaagctatt agtactttaa ggaaaggtgg ttttattca cagaaagtta    660 caactaatcc aaaccttagg atcatcagtc taaacacaaa cttgtactac ggcccaaata    720
taatgacact gaacaagact gacccagcca accagtttga atggctagaa agtacattga    780
acaactctca gcagaataag gagaaggtgt atatcatagc acatgttcca gtggggtatc    840
tgccatcttc acagaacatc acagcaatga gagaatacta taatgagaaa ttgatagata    900
tttttcaaaa atacagtgat gtcattgcag gacaattta tggacacact cacagagaca    960
gcattatggt tctttcagat aaaaaggaa gtccagtaaa ttctttgttt gtggctcctg    1020
ctgttacacc agtgaagagt gttttagaaa acagaccaa caatcctggt atcagactgt    1080
ttcagtatga tcctcgtgat tataaattat tggatatgtt gcagtattac ttgaatctga    1140
cagaggcgaa tctaaaggga gagtccatct ggaagctgga gtatatcctg acccagacct    1200
acgacattga agatttgcag ccggaaagtt tatatggatt agctaaacaa tttacaatcc    1260
tagacagtaa gcagtttata aaatactaca attacttctt tgtgagttat gacagcagtg    1320
taacatgtga taagacatgt aaggcctttc agatttgtgc aattatgaat cttgataata    1380
tttcctatgc agattgcctc aaacagcttt atataaagca caattactag tatttcacag    1440
```

```
tttttgctaa tagaaaatgc tgattctgat tctgagatca atttgtggga attttacata    1500
aatctttgtt aattactgag tgggcaagta gacttcctgt ctttgctttc tttttttttt    1560 tcttttgat gccttaatgt agatatcttt atcattctga attgtattat atatttaaag     1620
tgctcattaa tagaatgatg gatgtaaatt ggatgtaaat attcagttta tataattata    1680
tctaatttgt acccttgttg aaattgtcat ttatacaata aagcgaattc tttatctcta    1740
aatatgaaaa aaaaaaaaa aagg                                            1764

<210> SEQ ID NO 14
<211> LENGTH: 1621
<212> TYPE: DNA
<213> ORGANISM: Homo sapiens
<220> FEATURE:
<221> NAME/KEY: misc_feature
<223> OTHER INFORMATION: Incyte ID No: 2011230

<400> SEQUENCE: 14
ggagcagggc cgggcgccat ggcaccgtgg ggcaagcggc tggctggcgt gcgcggggtg    60
ctgcttgaca tctcgggcgt gctgtacgac agcggcgcgg gcggcggcac ggccatcgcc    120
ggctcggtgg aggcggtggc cagactgaag cgttcccggc tgaaggtgag gttctgcacc    180
aacgagtcgc agaagtcccg ggcagagctg gtggggcagc ttcagaggct gggatttgac    240
atctctgagc aggaggtgac cgccccggca ccagctgcct gccagatcct gaaggagcaa    300
ggcctgcgac catacctgct catccatgac ggagtccgct cagaatttga tcagatcgac    360
acatccaacc caaactgtgt ggtaattgca gacgcaggag aaagcttttc ttatcaaaac    420
atgaataacg ccttccaggt gctcatggag ctggaaaaac ctgtgctcat atcactggga    480
aaagggcgtt actacaagga gacctctggc ctgatgctgg acgttggtcc ctacatgaag    540
gcgcttgagt atgcctgtgg catcaaagcc gaggtggtgg ggaagccttc tcctgagttt    600
ttcaagtctg ccctgcaagc gataggagtg gaagcccacc aggccgtcat gattggggac    660
gatatcgtgg gcgacgtcgg cggtgcccag cggtgtggaa tgagagcgct gcaggtgcgc    720
accgggaagt tcaggcccag tgacgagcac catccggaag tgaaggctga tgggtacgtg    780
gacaacctcg cagaggcagt ggacctgctg ctgcagcacg ccgacaagtg atggcctcct    840
gggagaaccc cgcctcctcc acccctgcct ctcctccacc cctgcctccc ctccacccct    900
gcctcttctc cacccgccca ggagagcccc acctcctcca cccctgcctc tcctccaccc    960
ctgcctcccc tccacctgcc ccagtgccca gaccaaccaa ggccctgaca gccctgcctt    1020
ctgccctctg ccctgcatgg gcaggcattt gttccctacc tgggtggcct gctcccctgc    1080
ctgggccctg acttcagctc cctgtagtga agtccaggag ggtgggacag gcctgtcagg    1140
cctctgggaa tctcccaaat cccagaactc accactcacc atgggccttt aaatgcagta    1200
aactccacct aaccagattc aggggcacta tgcccactgc ctcctcttca gactctttgc    1260
atttcagtga agagcctgga agaaacccag gggcctccta tgcacagatc ttgcagccca    1320
gaaccaagtc agcctccctg cgactgccca ggcacactgc ccaccacccc acccccgaaa    1380
caatgccagc ccgctgcttt ttctatcctc ccagtcacct ttgcagacaa agaccagggg    1440
cagctcccga gggcactgtg aaggctccca tgccacacag tgagaactgt agcctctgcg    1500
tccaaggcac acagggtact ttctggaccc actgctggac agacttgaag gtgtcatgcc    1560
cggtgtgtgc aggaggaaac taacagttca gtaaactctg ccttgaccag caaaaaaaaa    1620
a                                                                    1621
```

<210> SEQ ID NO 15
<211> LENGTH: 1624
<212> TYPE: DNA
<213> ORGANISM: Homo sapiens
<220> FEATURE:
<221> NAME/KEY: misc_feature
<223> OTHER INFORMATION: Incyte ID No: 2768301

<400> SEQUENCE: 15

| | | | | | |
|---|---|---|---|---|---|
| tgcgggggcg | gccgagggg | aagagtgtgt | ctgcgggaga | aagaggagaa | tcgcccaagc | 60 |
| ggcctcggaa | gtcccaggga | gtggaggccc | ccgccgtgga | gccgtgtggt | gtatgtgtgg | 120 |
| taacaccatg | tctgtgcccc | tgctcaccga | tgctgccacc | gtgtctggag | ctgagcggga | 180 |
| aacggccgcg | gttattttt | tacatggact | tggagacaca | gggcacagct | gggctgacgc | 240 |
| cctctccacc | atccggctcc | ctcacgtcaa | gtacatctgt | ccccatgcgc | ctaggatccc | 300 |
| tgtgaccctc | aacatgaaga | tggtgatgcc | ctcctggttt | gacctgatgg | ggctgagtcc | 360 |
| agatgcccca | gaggacgagg | ctggcatcaa | gaaggcagca | gagaacatca | aggccttgat | 420 |
| tgagcatgaa | atgaagaacg | ggatccctgc | caatcgaatc | gtcctgggag | cttttcaca | 480 |
| gggcggggcc | ctgtccctct | acacggccct | cacctgcccc | caccctctgg | ctggcatcgt | 540 |
| ggcgttgagc | tgctggctgc | ctctgcaccg | ggccttcccc | caggcagcta | atggcagtgc | 600 |
| caaggacctg | gccatactcc | agtgccatgg | ggagctggac | cccatggtgc | ccgtacggtt | 660 |
| tggggccctg | acggctgaga | agctccggtc | tgttgtcaca | cctgccaggg | tccagttcaa | 720 |
| gacatacccg | ggtgtcatgc | acagctcctg | tcctcaggag | atggcagctg | tgaaggaatt | 780 |
| tcttgagaag | ctgctgcctc | ctgtctaact | agtcgctggc | cccagtgcag | taccccagct | 840 |
| catggggac | tcagcaagca | agcgtggcac | catcttggat | ctgagccggt | cgagcccctg | 900 |
| tccccaccct | tcctgacctg | tccttttccc | acaggcctct | gggggcaggt | ggcaaggcct | 960 |
| ggccgggcct | tccttcctgg | ccttagccac | ctggctctgt | ctgcagcagg | ggcaggctgc | 1020 |
| tttcttatcc | atttccctgg | aggcgggccc | ccctggcagc | agtattggag | gggctacagg | 1080 |
| cagctggaga | aagggggcca | gccgctgacc | cactcactca | ggacctcact | cactagcccc | 1140 |
| gctttgggcc | ccctcctgtg | acctcagggt | ttggcccatg | gggccctccc | aggccctgc | 1200 |
| cccaactgat | tctgcccaga | taatcgtgtc | tcctgcctcc | actcagctgc | ttctcagtca | 1260 |
| tgaatgtggc | catggcccg | gggtcccctt | gctgctgtgg | gctccctgtc | cctgggcagg | 1320 |
| agtgctggtg | aggaggtgga | gccttttgag | gggggccttc | cctcagctgt | tccccacac | 1380 |
| tggggggctg | ggccctgcct | cccgttacc | ctccttccct | gcaggcctgg | agcctgtagg | 1440 |
| gctggactga | ggttcaggtc | tcccccagc | tgtctcaccc | ccactttgtc | cccactctag | 1500 |
| agcagggagg | cagtggggga | ggagttgtgt | ctcgtcttct | gtctccatgt | ggttttttggg | 1560 |
| tgttttttctt | gttgtgtcct | ggattccgat | aaaattaaag | aaattgcttc | ctcaaaaaaa | 1620 |
| aaaa | | | | | | 1624 |

<210> SEQ ID NO 16
<211> LENGTH: 973
<212> TYPE: DNA
<213> ORGANISM: Homo sapiens
<220> FEATURE:
<221> NAME/KEY: misc_feature
<223> OTHER INFORMATION: Incyte ID No: 2886583

<400> SEQUENCE: 16

-continued

```
agccgtagcg cccggctcct gcaggcgctc ggcctccgct cattcctgac cccgcagtgg      60
gcgcgatggc ggaggctgta ctgagggtcg cccggcggca gctgagccag cgcggcgggt     120
ctggagcccc catcctcctg cggcagatgt tcgagcctgt gagctgcacc ttcacgtacc     180
tgctgggtga cagagagtcc cgggaggccg ttctgatcga cccagtcctg gaaacagcgc     240
ctcgggatgc ccagctgatc aaggagctgg ggctgcggct gctctatgct gtgaataccc     300
actgccacgc ggaccacatt acaggctcgg ggctgctccg ttccctcctc cctggctgcc     360
agtctgtcat ctcccgcctt agtggggccc aggctgactt acacattgag gatgcagact     420
ccatccgctt cgggcgcttc gcgttggaga ccagggccag ccctggccac accccaggct     480
gtgtcacctt cgtcctgaat gaccacagca tggccttcac tggagatgcc ctgttgatcc     540
gtgggtgtgg gcggacagac ttccagcaag gctgtgccaa gaccttgtac cactcggtcc     600
atgaaaagat cttcacactt ccaggagact gtctgatcta ccctgctcac gattaccatg     660
ggttcacagt gtccaccgtg gaggaggaga ggactctgaa ccctcggctc accctcagct     720
gtgaggagtt tgtcaaaatc atgggcaacc tgaacttgcc taaacctcag cagatagact     780
ttgctgttcc agccaacatg cgctgtgggg tgcagacacc cactgcctga tctcacttct     840
gtcagatgct cccatccact attaatgcac taggtgggag gagagggcgg caatgacact     900
gcacctctcc tttcccaccg cattccctgg agctccctaa ataaaacttt ttttatcgtg     960
aaaaaaaaaa aaa                                                        973
```

<210> SEQ ID NO 17
<211> LENGTH: 263
<212> TYPE: DNA
<213> ORGANISM: Homo sapiens
<220> FEATURE:
<221> NAME/KEY: misc_feature
<223> OTHER INFORMATION: Incyte ID No: 094168H1
<221> NAME/KEY: unsure
<222> LOCATION: 76, 88, 121, 167, 173, 185, 195, 219, 221, 234, 254, 257, 259
<223> OTHER INFORMATION: a, t, c, g, or other

<400> SEQUENCE: 17

```
agtgatccta atgctgtggt catgggattg gcaccagaac attttcatta tcaaattctg      60
aatcaagcat tccggntact cctggatnga gcacctctga tagcaatcca caaagccagg     120
nattacaaga ggaaaagatg gcttagcccc ggggcctgga ccatttntga ctncttttaga     180 gtatnccaca gatancaaag ccacagtcgt ggggtaaanc ngagaagacc gttnttttt     240 ggaagcattt cggnggnanc tag                                             263
```

<210> SEQ ID NO 18
<211> LENGTH: 293
<212> TYPE: DNA
<213> ORGANISM: Homo sapiens
<220> FEATURE:
<221> NAME/KEY: misc_feature
<223> OTHER INFORMATION: Incyte ID No: 2470694F6
<221> NAME/KEY: unsure
<222> LOCATION: 186
<223> OTHER INFORMATION: a, t, c, g, or other

<400> SEQUENCE: 18

```
gtcgggcagc agcggggctg tctatcccgg ctgaggaccc gcggccagtg cgggtggctg      60
gctttgccat tagcggggc ctttcctgag gacggcgtac ggagtgtggg gaatgaagga     120
tggcagcatg ccgtgcatta aaagctgttt tggtagatct cagtggcaca cttcacattg     180
```

| | |
|---|---|
| aagatncagc tgtgccaggc gcacaggaag ctcttaaaag gttacgtggt gcttctgtaa | 240 |
| tcattaggtt tgtgaccaat acaacccaaa gagagcaaag caagacctgt tag | 293 |

<210> SEQ ID NO 19
<211> LENGTH: 303
<212> TYPE: DNA
<213> ORGANISM: Homo sapiens
<220> FEATURE:
<221> NAME/KEY: misc_feature
<223> OTHER INFORMATION: Incyte ID No: 3595859H1

<400> SEQUENCE: 19

| | |
|---|---|
| taggtttgtg accaatacaa ccaaagagag caagcaagac ctgttagaaa ggttgagaaa | 60 |
| attggaattt gatatctctg aagatgaaat attcacatct ctgactgcag ccagaagttt | 120 |
| actagagcgg aaacaagtca gacccatgct gctagttgat gatcgggcac tacctgattt | 180 |
| caaaggaata caaacaagtg atcctaatgc tgtggtcatg ggattggcac cagaacattt | 240 |
| tcatatcaaa ttctgaatca agcattccgg ttactcctgg atggagcacc tctgatagca | 300 |
| tcc | 303 |

<210> SEQ ID NO 20
<211> LENGTH: 461
<212> TYPE: DNA
<213> ORGANISM: Homo sapiens
<220> FEATURE:
<221> NAME/KEY: misc_feature
<223> OTHER INFORMATION: Incyte ID No: 1864296F6
<221> NAME/KEY: unsure
<222> LOCATION: 178, 347
<223> OTHER INFORMATION: a, t, c, g, or other

<400> SEQUENCE: 20

| | |
|---|---|
| tccggttact cctggatgga gcacctctga tagcaatcca caaagccagg tattacaaga | 60 |
| ggaaagatgg cttagccctg gggcctggac catttgtgac tgctttagag tatgccacag | 120 |
| ataccaaagc cacagtcgtg gggaaaccag agaagacgtt cttttttggaa gcattgcngg | 180 |
| gcactggctg tgaacctgag gaggctgtca tgataggaga tgattgcagg gatgatgttg | 240 |
| gtggggctca agatgtcggc atgctgggca tcttagtaaa gactgggaaa tatcgagcat | 300 |
| cagatgaaga aaaaattaat ccacctcctt acttaacttg tgagagnttc cctccatgct | 360 |
| gtggaccaca ttctgcagca cctattgtga agcaatgtgt gcatctgaag caacttgaaa | 420 |
| tgcagcttct tattgtcctg gaatgaatcc cttaccaact c | 461 |

<210> SEQ ID NO 21
<211> LENGTH: 555
<212> TYPE: DNA
<213> ORGANISM: Homo sapiens
<220> FEATURE:
<221> NAME/KEY: misc_feature
<223> OTHER INFORMATION: Incyte ID No: 1864296T6
<221> NAME/KEY: unsure
<222> LOCATION: 547
<223> OTHER INFORMATION: a, t, c, g, or other

<400> SEQUENCE: 21

| | |
|---|---|
| aagaataatc catgctacaa gacgagattt cattttacag ctgtagtaac caagtgcata | 60 |
| aaagcttgaa tctgtcccaa tagcttctaa aaaattttc ccatagtgtc agaggcaaaa | 120 |
| ataatgaaat cttgcaaatg tacagttaat aggacctag tggacactaa cttcaaaaat | 180 |
| gcatggtcta taagatatta taaggcttga ttctagtttc tgcactgttc ctgttaataa | 240 |

-continued

| | |
|---|---|
| caatgtctaa ttaaaacatc tgtaaaatac tgatagtttt aatttttacat aaaatttcca | 300 |
| aaacaactgt tacacagtat aataggtatc tgcaatgaat aggttattaa tggaaatatt | 360 |
| aatttaaatt aaaatctggt tctaaattta aattagtcat ctctggctaa tgaagagaaa | 420 |
| aagaagtcac ccgtgctggg aatacagtag aaaatttagt tttcaacatc tggttaaagc | 480 |
| aaattcactg taccacttgg ggctaaagaa caattcacct ttgttgcttt ccggtcttct | 540 |
| ccatttnggc acatc | 555 |

<210> SEQ ID NO 22
<211> LENGTH: 475
<212> TYPE: DNA
<213> ORGANISM: Homo sapiens
<220> FEATURE:
<221> NAME/KEY: misc_feature
<223> OTHER INFORMATION: Incyte ID No: 1622192F6

<400> SEQUENCE: 22

| | |
|---|---|
| ggctcaagat gtcggcatgc tgggcatctt agtaaagact gggaaatatc gagcatcaga | 60 |
| tgaagaaaaa attaatccac ctccttactt aacttgtgag agtttccctc atgctgtgga | 120 |
| ccacattctg cagcacctat tgtgaagcaa tgtgtgcatc tgaagcaact gaaatgcag | 180 |
| cttcttattg tctggaatga atcccttacc aactcagtgc cagcatcggt agacaccagt | 240 |
| cagtgctgat cgcttttttaa ccctcttttg ttgtgcatta attagaaaga aaggtattga | 300 |
| attgcggcta gccagtaagc cttgctaatc tcttttatttt tgtaactgaa gatgagaccc | 360 |
| aaagaaaggg aaagctgaga ttttgtgcca ttcctttttaa aatattcatc aggttaggtg | 420 |
| gggctgtggg ggaaaagcta ctacagggag agtgttctct gctgtctctt cactg | 475 |

<210> SEQ ID NO 23
<211> LENGTH: 526
<212> TYPE: DNA
<213> ORGANISM: Homo sapiens
<220> FEATURE:
<221> NAME/KEY: misc_feature
<223> OTHER INFORMATION: Incyte ID No: 1695044F6
<221> NAME/KEY: unsure
<222> LOCATION: 375
<223> OTHER INFORMATION: a, t, c, g, or other

<400> SEQUENCE: 23

| | |
|---|---|
| ctgtgaagaa agttgaatgg tggtttttaa attataaagt aatgtattaa aaggtgcatt | 60 |
| aggctgtagt tctaatattg agttcaactg tgaaatccat cagatgtgcc aaatggagaa | 120 |
| gacagaaagc aacaaagtga attgttcttt agcccaagtg gtacagtgaa tttgctttaa | 180 |
| cagatgttga aaactaaatt ttctactgta ttcccagcac gggtgacttc tttttctctt | 240 |
| cattagccag agatgactaa tttaaattta gaaccagatt ttaatttaaa ttaatatttc | 300 |
| cattaataac ctattcattg cagataccta ttatactgtg taacagttgt tttggaaatt | 360 |
| ttatgtaaaa ttaanactat cagtattta ccagatgttt aattagaca ttgttattaa | 420 |
| caggaacagt gcagaaacta gaatcaagcc ttataatatc ttatagacca tgcatttga | 480 |
| agttagtgtc cactaagggt cctattaact gtacatttgc aagatt | 526 |

<210> SEQ ID NO 24
<211> LENGTH: 630
<212> TYPE: DNA
<213> ORGANISM: Homo sapiens
<220> FEATURE:
<221> NAME/KEY: misc_feature
<223> OTHER INFORMATION: Incyte ID No: 1431642T1

```
<221> NAME/KEY: unsure
<222> LOCATION: 4, 26, 549, 616
<223> OTHER INFORMATION: a, t, c, g, or other

<400> SEQUENCE: 24
ctancattta tttagctttg ttcccnccca tcctaagact gctgatctct aaacaagcat    60
caaaacccga agctcattaa catcagagtg agcttcaata aggtgaacac tacaatgatg   120
tacaattaca tcctaataat tcaatgccca agagccctgt agaactattg caaggcccag   180
gattatcaca gtatgcaaat gcactaggaa aatcattacc tatttagtcc ctttatttt    240 ggtgggttta acatgagaag aataatccat gctacaagac gagatttcat tttacagctg   300
tagtaaccaa gtgcataaaa gcttgaatct gtcccaatag cttctaaaaa attttccca    360 tagtgtcaga ggcaaaaata atgaaatctt gcaaatgtac agttaatagg accctagtgg   420
acactaactt caaaaatgca tggctataag atattataag gcttgattct agtttctgca   480
ctgttcctgt taataacaat gtctaattaa aacatctgta aaatactgat agttttaatt   540
ttacataana tttccaaaac aactgttaca cagtataata ggtactgcaa tgaataggtt   600
attaatggaa tattanttta aattaaatct                                   630

<210> SEQ ID NO 25
<211> LENGTH: 543
<212> TYPE: DNA
<213> ORGANISM: Homo sapiens
<220> FEATURE:
<221> NAME/KEY: misc_feature
<223> OTHER INFORMATION: Incyte ID No: 195647R1
<221> NAME/KEY: unsure
<222> LOCATION: 71, 289, 336, 389, 411, 444, 509, 521-522, 537
<223> OTHER INFORMATION: a, t, c, g, or other

<400> SEQUENCE: 25
cggatgagga tacagaaggc tggaggaaac gtcaggatgg gcgtgttttg ggcgtgctag    60
aggtgtcacg ntccattggg gacgggccag tacaagcgct gcggtgtcac ctctgtgccc   120
gacatcagac gctgccagct gaccccaat gacaggttca ttttgttggc ctgtgatggg   180
ctcttcaagg tctttacccc agaagaagcc gtggaacttc atcttgtcct gtctcgagga   240
tgaaaagatc cagacccggg aagggaagtc cgcagccgac gcccgctang aagcagcctg   300
caacaggctg gccaacaagg cggtgcagcg gggctnggcc gacaacgtca ctgtgatggt   360
ggtgcggata gggcactgag gggtggcgng cggccagggg cacgcatggt nttgacttaa   420
aaggttcatt ttgtgtgtgt gcanattgtg tgttttgtgt actcctgtgg gacttccatg   480
gttgtaaata aaggtttctc tttttttttnc ctaaaaaaaa nnaaaaaaaa aactcgnggg   540
ggg                                                                543

<210> SEQ ID NO 26
<211> LENGTH: 266
<212> TYPE: DNA
<213> ORGANISM: Homo sapiens
<220> FEATURE:
<221> NAME/KEY: misc_feature
<223> OTHER INFORMATION: Incyte ID No: 1795063H1
<221> NAME/KEY: unsure
<222> LOCATION: 5, 38, 123
<223> OTHER INFORMATION: a, t, c, g, or other

<400> SEQUENCE: 26
ccgcncgccc ggggtgtgga gcccggccgc tgctcgcngg ctgagtgtct gtcgctgctg    60
ccgcctccac ccagcctccg ccatggacct cttcggggac ctgccggagc ccagcgctc   120
```

```
gcngcgcccg gctgccggga agaagctca gaaaggaccc ctgctctttg atgacctccc    180
tccggccagc agtactgact caggatcagg gggacctttg ctttttgatg atctcccacc    240
cgctagcagt ggcgattcag gttctc                                         266
```

<210> SEQ ID NO 27
<211> LENGTH: 563
<212> TYPE: DNA
<213> ORGANISM: Homo sapiens
<220> FEATURE:
<221> NAME/KEY: misc_feature
<223> OTHER INFORMATION: Incyte ID No: 1813266F6

<400> SEQUENCE: 27

```
gggaaaggag caaagagaaa aacctccgag gaagagaaga atggcagtga agagcttgtg     60
gaaaagaaac ctcttcggtg atctttggtc tgaagggcta tgtggctgag cggaaggggtg   120 agagggagga gatgcaggat gcccacgtca tcctgaacga catcaccgag gagtgtaggc    180
ccccatcgtc cctcattact cgggtttcat attttgctgt ttttgatgga catggaggaa    240
ttcgagcctc aaaatttgcc gcacagaatt tgcatcaaaa cttaatcaga aaatttccta    300
aaggagatgt aatcagtgta gagaaaaccg tgaagagatg ccttttggac actttcaagc    360
atactgatga agagttcctt aaacaagctt ccagccagaa gcctgcctgg aaagatgggt    420
ccactgccac gtgtgttctg gctgtagaca acattcttta tattgccaac ctcggagata    480
gtcgggcaat cttgtgtcgt tataatgagg agagtcaaaa acatgcagct taagctcagc    540
aaagagcata atccaactca gta                                            563
```

<210> SEQ ID NO 28
<211> LENGTH: 934
<212> TYPE: DNA
<213> ORGANISM: Homo sapiens
<220> FEATURE:
<221> NAME/KEY: misc_feature
<223> OTHER INFORMATION: Incyte ID No: 728148X27
<221> NAME/KEY: unsure
<222> LOCATION: 2, 4, 7, 10, 12, 49, 69, 100, 135, 241, 243, 255, 261,
      286, 320, 330, 333,
<223> OTHER INFORMATION: a, t, c, g, or other

<400> SEQUENCE: 28

```
gnangcnatn cnggatgccc acgtcatcct gaacgacatc accgaggant gtaggccccc     60
atcgtcccnc attactcggg tttcatattt tgctgttttn gatggacatg gaggaattcg    120
agcctcaaaa tttgntgcac agaatttgca tcaaaactta atcagaaaat ttcctaaagg    180
agatgtgatc agtgtagaga aaaccgtgaa gagatgcctt tggacactt tcaagcatac    240 ngntgaagag ttccntaaac nagcttccag ccagaagcct gctgnaaaa atgggtccac    300 tgccacgtgt gttctggctn tagacaacan tcnttatatt gcnaccctcg agatagtcg    360 gggcnatctt gtgtcgttag anatgaggga gagtcaaaaa catgacagcc ttaaaggncc    420
ccagcaaaga gncgtaatcc aactgcngta tgaaggaang gatgaggant acanaagggc    480
tggnggagan gtacanttgg gggccnancc aanggngtta ngnnctccct tgggaggcgg    540
ggangntgaa gatttgtggt gntncctgcg nngggngggg ggnggagcgc acangggngg    600
gacccngctn acaggggccn gttgatgggc gcgtgatagg ntcttccaag ganttaacc    660 cggaaagaan cnnganctnc anncctgggnt gttccacgga gncgcannnt tcanaacccg    720
ggangnnnag tccgncggcn gacgncngnt tannanngcag cntgaaaaag gtngccacca    780
```

-continued

| | |
|---|---|
| nggnggtgan ngnggtccga cngaaangta nccgtgatgg tgtccgatag ggcctgaagg | 840 |
| ggtgctnnct gcnggncacn anggcatgnn taaaaggtcn tttggtgggg acaataggtn | 900 |
| tngggaaccg ggggccccccn ggtgnaanan gntt | 934 |

<210> SEQ ID NO 29
<211> LENGTH: 181
<212> TYPE: DNA
<213> ORGANISM: Homo sapiens
<220> FEATURE:
<221> NAME/KEY: misc_feature
<223> OTHER INFORMATION: Incyte ID No: 507537X14
<221> NAME/KEY: unsure
<222> LOCATION: 6-7, 9, 25-26, 46, 51, 53, 78, 81, 84, 89, 171-172
<223> OTHER INFORMATION: a, t, c, g, or other

<400> SEQUENCE: 29

| | |
|---|---|
| gtcgtnncna ttacaaaaag gggcnncgag ccaaaattcg aagttntagt ntnctggatc | 60 |
| accgtgaagg aagtggandct nccngcctnt gcccacaaga gaatgacacc atcttccatg | 120 |
| cttaccacag ggaggcaagc tcaatgtaca tcttatttca ttgaacctgt nncaaagggg | 180 |
| g | 181 |

<210> SEQ ID NO 30
<211> LENGTH: 245
<212> TYPE: DNA
<213> ORGANISM: Homo sapiens
<220> FEATURE:
<221> NAME/KEY: misc_feature
<223> OTHER INFORMATION: Incyte ID No: 868893H1
<221> NAME/KEY: unsure
<222> LOCATION: 2
<223> OTHER INFORMATION: a, t, c, g, or other

<400> SEQUENCE: 30

| | |
|---|---|
| gncgccttgt ctctgggcgc ggccatgttg gaggctccgg gcccgagtga tggctgcgag | 60 |
| ctcagcaacc ccagcgccag cagagtcagc tgtgccgggc agatgctgga agtgcagcca | 120 |
| ggattgtatt tcggtggggc cgcggccgtc gcggagccag atcacctgag ggaagcgggc | 180 |
| atcacggccg tgctaacagt ggactcggag gagcccagct tcaaggcggg gcctggggtc | 240 |
| gagga | 245 |

<210> SEQ ID NO 31
<211> LENGTH: 464
<212> TYPE: DNA
<213> ORGANISM: Homo sapiens
<220> FEATURE:
<221> NAME/KEY: misc_feature
<223> OTHER INFORMATION: Incyte ID No: 2272231R6
<221> NAME/KEY: unsure
<222> LOCATION: 121, 414
<223> OTHER INFORMATION: a, t, c, g, or other

<400> SEQUENCE: 31

| | |
|---|---|
| cgctggacaa acccgagacg gacctactca gccatctgga ccggtgcgtg gccttcatcg | 60 |
| gtcaggcccg cgctgagggc cgtgcggtgt tggtgcactg tcatgcagga gtcagtcgaa | 120 |
| ntgtggccat aataactgct tttctcatga agactgacca acttcccttt gaaaagcct | 180 |
| atgaaaagct ccagattctc aaaccagagg ctaagatgaa tgaggggttt gagtggcaac | 240 |
| tgaaattata ccaggcaatg ggatatgaag tggataccctc tagtgcaatt tataagcaat | 300 |
| atcgtttaca aaaggttaca gagaagtatc cagaattgca gaatttacct caagaactct | 360 |
| ttgctgttga cccaactacc gtttcacaag gattgaaaga tgaggttctc tacnagtgta | 420 |

```
gaaagtgcag gcgatcatta tttcgagttc tagtattctg gatc            464
```

<210> SEQ ID NO 32
<211> LENGTH: 448
<212> TYPE: DNA
<213> ORGANISM: Homo sapiens
<220> FEATURE:
<221> NAME/KEY: misc_feature
<223> OTHER INFORMATION: Incyte ID No: 2379239F7
<221> NAME/KEY: unsure
<222> LOCATION: 394, 416, 438
<223> OTHER INFORMATION: a, t, c, g, or other
<400> SEQUENCE: 32

```
ataattttaa gaaaatgaaa ctttatattt cttatcatt acaggatgaa tgagggttt       60 gagtggcaac tgaaattata ccaggcaatg ggatacgaag tggataccctc tagtgcaatt     120 tataagcaat atcgtttaca aaaggttaca gagaagtatc cagaattgca gaatttacct    180
caagaactct tgctgttga cccaactacc gtttcacaag gattgaaaga tgaggttctc     240
tacaagtgta gaaagtgcag gcgatcatta tttcgaagtt ctagtattct ggatcaccgt   300
gaaggaagtg gacctatagc ctttgcccac aagagaatga caccatcttc catgcttacc   360
acagggaggc aagctcaatg taccatctta ttcnatgaac ctgtacagtg ggaggnatct    420
gctttgttgg gagtgatnga tggacagc                                        448
```

<210> SEQ ID NO 33
<211> LENGTH: 113
<212> TYPE: DNA
<213> ORGANISM: Homo sapiens
<220> FEATURE:
<221> NAME/KEY: misc_feature
<223> OTHER INFORMATION: Incyte ID No: 1397852F1

<400> SEQUENCE: 33

```
tttcatttga aatgggagaa gataaaatca cttgatgtaa cctggaaact atgctttaca     60
tggcaatcaa agccttttga tcatgtacat tttatttgat attaaaatct ttt            113
```

<210> SEQ ID NO 34
<211> LENGTH: 765
<212> TYPE: DNA
<213> ORGANISM: Homo sapiens
<220> FEATURE:
<221> NAME/KEY: misc_feature
<223> OTHER INFORMATION: Incyte ID No: 971204X37
<221> NAME/KEY: unsure
<222> LOCATION: 3-4, 8, 13, 15-16, 18, 20-22, 37, 44, 46, 48-49, 60, 68,
      307, 327, 339,
<223> OTHER INFORMATION: a, t, c, g, or other
<400> SEQUENCE: 34

```
ctnngggntc aantnntngn nncgctggag ccaaccngct ccgnanannt ccttagtgcn     60
ttgtgctntg ggcgtgagcc gatccgccac cctggtactg gcctacctca tgctgtacca    120
ccaccttacc ctcgtggagg ccatcaagga aagtcaaaga ccaccgaggc atcatcccca    180
accggggctt cctgaggcag ctcctggccc tggaccgcag gctgcggcag ggtctggaat   240
catgagggga gggggagaga ggtcaggcca ggcccgtggg tagtccctgg ctcccagctg    300
gacatangac gcccaggtgg caggtancag gaggcccana tcacccatcc tcccctgggg   360
tcagganagg ccgatcccca tgccactgtc actctttgcg ggaggggacg gggagtgagg    420
ttgggcantn tggtggatgg gcacccagga aaggttgacc agggaaggag gcagctaggc    480
```

-continued

```
tgtagatgga agatggtcct gggattcgaa caccgctggg atctggctan ggtgctccct    540
gggatcnaaa gtcccttccc ctctttgtgc ccaagtgttt ccctctctcc ctcaccaaaa    600
caaaaggcca tctcttccct gcacttgtnc agaaatcagg gatacngcaa gcatgaatgc    660
aatggtgtta aattgtnttg aaaccctagc atnganacng acagcgaaga aatggtgtna    720
aaagcttgca gaaccagaca ganaacccac agacttccac tccaa                   765
```

<210> SEQ ID NO 35
<211> LENGTH: 529
<212> TYPE: DNA
<213> ORGANISM: Homo sapiens
<220> FEATURE:
<221> NAME/KEY: misc_feature
<223> OTHER INFORMATION: Incyte ID No: 2822470F6
<221> NAME/KEY: unsure
<222> LOCATION: 324, 498
<223> OTHER INFORMATION: a, t, c, g, or other

<400> SEQUENCE: 35

```
cacgcatgca ttccaggcgg tgctgctggg gctcggcggg gccgtgtctg gtctgcaagg     60
cgcgcgggct cgtgggggt tggctgggga gcccacgctg cctggcgact cgggccaccg    120
aatgtgagac cgagtcccctt tatgtcacca gcgcacacgc tgatttgaac cctgcttcga   180
cgtgtgtgtc atggcttaaa aatagctgct aatctgtcaa cctgtcttgg gcagaaacag   240
cggcggcgac agcagcagga gcgtcatggc cgtggcgctg tctgcgccgg cgatccgcct   300
ttcggactga ggcccagcgc accnttgcaa agagcagcag ctacctggca actgaaccca   360
tcatcaccac agccactcct gcagctgcca cggtttctgc cacctctaag atgtgccctg   420
gtaactggct ttgggcttct atgacttta tggcccgctt ctcccggagt agctcaaggt    480
ctcctgttcg aactcgangg acctggaaga gatgccaacc gttcaacat                529
```

<210> SEQ ID NO 36
<211> LENGTH: 629
<212> TYPE: DNA
<213> ORGANISM: Homo sapiens
<220> FEATURE:
<221> NAME/KEY: misc_feature
<223> OTHER INFORMATION: Incyte ID No: STEQ00223R1
<221> NAME/KEY: unsure
<222> LOCATION: 8, 10, 12-13, 19, 23, 31, 38-43, 47-48, 53, 65, 68, 73,
      85, 90, 92, 96-97,
<223> OTHER INFORMATION: a, t, c, g, or other

<400> SEQUENCE: 36

```
tggctctncn anncatgcna canatcttta natattcnnn nnngtcnngc cangcctcta     60
tctcnganac cangacatgg ctaanaaccn cngggnngtt acngnctngn catcacntca    120
cgtcctcaat gcctcacaca gcnnttttnn ntncacgcnc gaggcctatt ntgggctggg    180
natccgctac ctgggtgttg agccagcctt tgacatgagc atccacttcc agannnctgc    240
cgacttcatc caccgggcgc tnagccagcc aggagggaag atcctggtnc attgtgctgt    300
ggnnttnagc gatccgccaa cctggtactg gcctanctca tgctgtacca cacccttancc   360 tngtggaggc natnaagaaa ttcaaagacc acngaggntc atcccnaacc ggggnttcct    420
taggaagncc tggccctgga acgaagntnn ggcanggttg gaagcattaa gggatgggga    480
aaaaangtta agncaaggcc cnttggtaag ttnccttggn ttccaaactt ggaagaataa    540
ngaangncca aantttgcaa ggtaancaag gaagggcccc aagatttaan ccaatncttn    600 cccccttgggg gttnaangaa aaanggccc                                     629
```

<210> SEQ ID NO 37
<211> LENGTH: 407
<212> TYPE: DNA
<213> ORGANISM: Homo sapiens
<220> FEATURE:
<221> NAME/KEY: misc_feature
<223> OTHER INFORMATION: Incyte ID No: STEQ02003R1
<221> NAME/KEY: unsure
<222> LOCATION: 5, 134, 235
<223> OTHER INFORMATION: a, t, c, g, or other

<400> SEQUENCE: 37

| | | | | | |
|---|---|---|---|---|---|
| gatcngcggc | cgccgaacac | cgctgggatc | tggctagggt | gctccctggg | attcacagtc | 60 |
| ccttcccctc | tttgtgccca | agtgtttccc | tctctccctc | accaaaacaa | aagggccatc | 120 |
| tctgccctgc | aatntcacag | aaagtcaggg | atacggcaag | catgaatgca | atggtgtaga | 180 |
| gttgtgtgaa | accoctagca | tagagacaga | cagcgaagag | atggtgtgaa | aagcntgcag | 240 |
| aaccagacag | agaaccccac | agactttcca | ctccaagcac | aggaggaggt | agctagcgtg | 300 |
| tgagggttgg | cactaggccc | acggctgctg | cttgggccaa | aaacatacag | aggtgcatgg | 360 |
| ctggcagtct | tgaaattgtc | actcgcttac | tggatccaag | tgtctcg | | 407 |

<210> SEQ ID NO 38
<211> LENGTH: 306
<212> TYPE: DNA
<213> ORGANISM: Homo sapiens
<220> FEATURE:
<221> NAME/KEY: misc_feature
<223> OTHER INFORMATION: Incyte ID No: 1376382F6

<400> SEQUENCE: 38

| | | | | | |
|---|---|---|---|---|---|
| gttttttgcta | atagaaaatg | ctgattctga | ttctgagatc | aatttgtggg | aattttacat | 60 |
| aaatctttgt | taattactga | gtgggcaagt | agacttcctg | tctttgcttt | cttttttttt | 120 |
| tcttttttgat | gccttaatgt | agatatcttt | atcattctga | attgtattat | atatttaaag | 180 |
| tgctcattaa | tagaatgatg | gatgtaaatt | ggatgtaaat | attcagttta | tataattata | 240 |
| tctaatttgt | acccttgttg | aaattgtcat | ttatacaata | aagcgaattc | tttatctcta | 300 |
| aatatg | | | | | | 306 |

<210> SEQ ID NO 39
<211> LENGTH: 610
<212> TYPE: DNA
<213> ORGANISM: Homo sapiens
<220> FEATURE:
<221> NAME/KEY: misc_feature
<223> OTHER INFORMATION: Incyte ID No: SAEA03372R1
<221> NAME/KEY: unsure
<222> LOCATION: 158, 254, 334, 569, 602
<223> OTHER INFORMATION: a, t, c, g, or other

<400> SEQUENCE: 39

| | | | | | |
|---|---|---|---|---|---|
| ctcaggcctg | acggtccgag | tggagctgcg | ggacagcccg | aacctccagg | tcagccccgc | 60 |
| ggccctccat | ggcgctggtg | cgcgcactcg | tctgctgcct | gctgactgcc | tggcactgcc | 120 |
| gctccggcct | cgggctgccc | gtggcgcccg | caggcggnca | ggaatcctcc | tccggcgata | 180 |
| ggacagttttt | ggcatgtgac | tgacttacac | ttagacccta | cttaccacat | cacagatgac | 240 |
| cacacaaaag | tgtntgcttc | atctaaaggt | gcaaatgcct | ccaaccctgg | cccttttgga | 300 |
| gatgttctgt | gtgattctcc | atatcaactt | attntgtcag | catttgattt | tattaaaaat | 360 |
| tctggacaag | aagcatcttt | catgatatgg | acaggggata | gcccacctca | tgttcctgta | 420 |

-continued

| cctgaactct caacagagca ctgttataaa tgtgatcact aatatgacaa ccaccatcca | 480 |
| gagtctcttt ccaaatctcc aggttttccc tgcgctgggt aatcatgact attgggccac | 540 |
| aggatcaact ggcctgtagt caccagtana gtgtacaatg cagtagcaaa cctctgggaa | 600 |
| ancatgggct | 610 |

<210> SEQ ID NO 40
<211> LENGTH: 379
<212> TYPE: DNA
<213> ORGANISM: Homo sapiens
<220> FEATURE:
<221> NAME/KEY: misc_feature
<223> OTHER INFORMATION: Incyte ID No: SAEA02307F1
<221> NAME/KEY: unsure
<222> LOCATION: 2-4, 14-15, 21, 24, 26, 30-32, 34, 38, 41, 44, 49,
    51-52, 60-61, 63-64, 66,
<223> OTHER INFORMATION: a, t, c, g, or other

<400> SEQUENCE: 40

| gnnntataga aganntatga ngtngnatgn nngngtangt nagnttggnt nntctagagn | 60 |
| ngnngnggtn tgtttttata naanantctt aantggtgta ntagnangag tannnnnann | 120 |
| nnnttgnnng gacttccttt tttatctgaa agaaccataa tgctgtctct gtgagtgtgt | 180 |
| ccataaaatt gtcctgcaat gacatcactg tattttgaa aaatatctat caatttctca | 240 |
| ttatagtatt ctctcattgc tgtgatgttc tgtgaagatg gcagatacccc cactggaaca | 300 |
| tgtgctatga tatacacctt ctccttattc tgctgagagt tgttcaatgt actttctagc | 360 |
| cattcaaact ggttggctg | 379 |

<210> SEQ ID NO 41
<211> LENGTH: 317
<212> TYPE: DNA
<213> ORGANISM: Homo sapiens
<220> FEATURE:
<221> NAME/KEY: misc_feature
<223> OTHER INFORMATION: Incyte ID No: SAEA02307R1

<400> SEQUENCE: 41

| acccagccaa ccagtttgaa tggctagaaa gtacattgaa caactctcag cagaataagg | 60 |
| agaaggtgta tatcatagca catgttccag tggggtatct gccatcttca cagaacatca | 120 |
| cagcaatgag agaatactat aatgagaaat tgatagatat ttttcaaaaa tacagtgatg | 180 |
| tcattgcagg acaattttat ggacacactc acagagacag cattatggtt ctttcagata | 240 |
| aaaaggaag tccagtaaat tctttgtttg tggctcctgc tgttacacca gtgaagagtg | 300 |
| ttttagaaaa acagacc | 317 |

<210> SEQ ID NO 42
<211> LENGTH: 463
<212> TYPE: DNA
<213> ORGANISM: Homo sapiens
<220> FEATURE:
<221> NAME/KEY: misc_feature
<223> OTHER INFORMATION: Incyte ID No: SAEA02991R1
<221> NAME/KEY: unsure
<222> LOCATION: 235-264, 439, 448, 455, 461
<223> OTHER INFORMATION: a, t, c, g, or other

<400> SEQUENCE: 42

| gttatgacag cagtgtaaca tgtgataaga catgtaaggc ctttcagatt tgtgcaatta | 60 |
| tgaatcttga taatatttcc tatgcagatt gcctcaaaca gctttatata aagcacaatt | 120 |
| actagtattt cacagttttt gctaatagaa aatgctgatt ctgattctga gatcaatttg | 180 |

```
tgggaattttt acataaatct ttgttaatta ctgagtgggc aagtagactt cctgnnnnnn        240
nnnnnnnnnn nnnnnnnnnn nnnngatgcc ttaatgtaga tatctttatc attctgaatt        300
gtattatata tttaaagtgc tcattaatag aatgatggat gtaaattgga tgtaaatatt        360
cagtttatat aattatatct aatttgtacc cttgttgaaa ttgtcattta taccaataaa        420
gcgaattctt tatctctana aaaaaganaa aatanaataa ngg                         463
```

<210> SEQ ID NO 43
<211> LENGTH: 404
<212> TYPE: DNA
<213> ORGANISM: Homo sapiens
<220> FEATURE:
<221> NAME/KEY: misc_feature
<223> OTHER INFORMATION: Incyte ID No: 2011230R6

<400> SEQUENCE: 43

```
caggagtccg ctcagaattt gatcagatcg acacatccaa cccaaactgt gtggtaattg         60
cagacgcagg agaaagcttt tcttatcaaa acatgaataa cgccttccag gtgctcatgg        120
agctggaaaa acctgtgctc atatcactgg gaaaagggcg ttactacaag gagacctctg        180
gcctgatgct ggacgttggt ccctacatga aggcgcttga gtatgcctgt ggcatcaaag        240
ccgaggtggt ggggaagcct tctcctgagt ttttcaagtc tgccctgcaa gcgataggag        300
tggaagccca ccaggccgtc atgattgggg acgatatcgt gggcgacgtc ggcggtgccc        360
agcggtgtgg aatgagagcg ctgcaggtgc gcaccgggaa gttc                        404
```

<210> SEQ ID NO 44
<211> LENGTH: 263
<212> TYPE: DNA
<213> ORGANISM: Homo sapiens
<220> FEATURE:
<221> NAME/KEY: misc_feature
<223> OTHER INFORMATION: Incyte ID No: 2855308H1
<221> NAME/KEY: unsure
<222> LOCATION: 19, 116
<223> OTHER INFORMATION: a, t, c, g, or other

<400> SEQUENCE: 44

```
cgtcggttgg gacgcggant gaggagcagg gccgggcgcc atggcaccgt ggggcaagcg         60
gctggctggc gtgcgcgggg tgctgcttga catctcgggc gtgctgtacg acagcngcgc        120
gggcggcggc acggccatcg ccggctcggt ggaggcggtg gccagactga agcgttcccg        180
gctgaaggtg aggttctgca ccaacgagtc gcagaagtcc cgggcagagc tggtgggggca       240 gcttcagagg ctgggatttg aca                                               263
```

<210> SEQ ID NO 45
<211> LENGTH: 451
<212> TYPE: DNA
<213> ORGANISM: Homo sapiens
<220> FEATURE:
<221> NAME/KEY: misc_feature
<223> OTHER INFORMATION: Incyte ID No: 1706605F6
<221> NAME/KEY: unsure
<222> LOCATION: 75, 90, 99, 132, 291, 357, 360, 369, 389, 402, 415-416,
       420, 429
<223> OTHER INFORMATION: a, t, c, g, or other

<400> SEQUENCE: 45

```
ggagcagggc cgggcgccat ggcaccgtgg ggcaagcggc tggctggcgt gcgcggggtg         60
ctgcttgaca tctcnggcgt gctgtacgan agcggcgcng gcggcggcac ggccatcgcc        120
```

-continued

| | |
|---|---|
| ggctcggtgg angcggtggc cagactgaag cgttcccggc tgaaggtgag gttctgcacc | 180 |
| aacgagtcgc agaagtcccg ggcagagctg gtggggcagc ttcagaggct gggatttgac | 240 |
| atctctgagc aggaggtgac cgccccggca ccagctgcct gccagatcct naaggagcga | 300 |
| ggcctgcgac catacctgct catccatgac ggagtccgct cagaatttga tcagatngan | 360 |
| acatccaanc caaactgtgt ggtaattgna dacgcaggag tnaagctttt cttanncaan | 420 |
| acatgaatna cgccttccag gtggctccat g | 451 |

<210> SEQ ID NO 46
<211> LENGTH: 481
<212> TYPE: DNA
<213> ORGANISM: Homo sapiens
<220> FEATURE:
<221> NAME/KEY: misc_feature
<223> OTHER INFORMATION: Incyte ID No: 1482295F6
<221> NAME/KEY: unsure
<222> LOCATION: 154, 156, 167, 174, 184-186, 189, 191, 193, 196-197,
    206, 209-210, 225,
<223> OTHER INFORMATION: a, t, c, g, or other

<400> SEQUENCE: 46

| | |
|---|---|
| actcgccctg tggaaggagc atacagtggg agatggggac aggcccagtg acgagcacca | 60 |
| tccggaagtg aaggctgatg ggtacgtgga caacctcgca gagcagtgga cctgctgctg | 120 |
| cagcacgccg acaagtgatg gcctcctggg agancnccgc ctcctcnacc cctncctctc | 180 |
| ctcnnnccnt ncntcnnctc caccnttnn tcttctccac ccgcncagga gancnccanc | 240 |
| tcctccancc ntgcntctnc tccanccctg cntccctcc acctgcncca gtgcncagac | 300 |
| caaccaaggn cctgacagnn ctgccttctg ccctctgnnc tgcatgggca ggcatttgtt | 360 |
| ccctacctgg gtggcctgct cccctgcctg ngnntnnttt cagntccntg aagtgaagtc | 420 |
| caggagngtg ggacaggctg tnaggctctg ggaatctccc aaatcccaga actcacactc | 480 |
| a | 481 |

<210> SEQ ID NO 47
<211> LENGTH: 496
<212> TYPE: DNA
<213> ORGANISM: Homo sapiens
<220> FEATURE:
<221> NAME/KEY: misc_feature
<223> OTHER INFORMATION: Incyte ID No: 1481157T6
<221> NAME/KEY: unsure
<222> LOCATION: 5, 14, 215-217, 306
<223> OTHER INFORMATION: a, t, c, g, or other

<400> SEQUENCE: 47

| | |
|---|---|
| tgaantgtta gttncacctg cacacacctg ggcatgacac cttcaagtct gtccagcagt | 60 |
| gggtccagaa agtaccctgt gtgccttgga cgcagaggct acagttctca ctgtgtggca | 120 |
| tgggagcctt cacagtgccc tcgggagctg cccctggtct ttgtctgcaa aggtgactgg | 180 |
| gaggatagaa aaagcagcgg gctggcattg tttcnnnggt ggggtggtgg gcagtgtgcc | 240 |
| tgggcagtcg cagggaggct gacttggttc tgggctgcaa gatctgtgca taggaggccc | 300 |
| ctgggnttct tccaggctct tcactgaaat gcaaagagtc tgaagaggag gcagtgggca | 360 |
| tagtgcccct gaatctggtt aggtggagtt tactgcattt aaaggcccat ggtgagtggt | 420 |
| gagttctggg atttgggaga ttcccagagg cctgacaggc tgtcccaccc tcctggactt | 480 |
| cactacaggg agctga | 496 |

<210> SEQ ID NO 48

```
<211> LENGTH: 260
<212> TYPE: DNA
<213> ORGANISM: Homo sapiens
<220> FEATURE:
<221> NAME/KEY: misc_feature
<223> OTHER INFORMATION: Incyte ID No: 2768301H1

<400> SEQUENCE: 48
gggaagagtg tgtctgcggg agaaagagga gaatcgccca agcggcctcg gaagtcccag      60
ggagtggagg cccccgccgt ggagccgtgt ggtgtatgtg tggtaacacc atgtctgtgc     120
ccctgctcac cgatgctgcc accgtgtctg agctgagcg ggaaacggcc gcggttattt     180
ttttacatgg acttggagac acagggcaca gctgggctga cgccctctcc accatccggc     240
tccctcacgt caagtacatc                                                 260

<210> SEQ ID NO 49
<211> LENGTH: 559
<212> TYPE: DNA
<213> ORGANISM: Homo sapiens
<220> FEATURE:
<221> NAME/KEY: misc_feature
<223> OTHER INFORMATION: Incyte ID No: 1582462F6
<221> NAME/KEY: unsure
<222> LOCATION: 34, 521
<223> OTHER INFORMATION: a, t, c, g, or other

<400> SEQUENCE: 49 gcggggggcgg ccgaggggga agagtgtgtc tgcnggagaa agaggagaat cgcccaagcg     60
gcctcggaag tcccagggag tggaggcccc cgccgtggag ccgtgtggtg tatgtgtggt    120
aacaccatgt ctgtgcccct gctcaccgat gctgccaccg tgtctggagc tgagcgggaa    180
acggccgcgg ttattttttt acatggactt ggagacacag gcacagctg gctgacgcc     240 ctctccacca tccggctccc tcacgtcaag tacatctgtc cccatgcgcc taggatccct    300
gtgaccctca acatgaagat ggtgatgccc tcctggtttg acctgatggg gctgagtcca    360
gatgccccag aggacgaggc tggcatcaag aaggcagcag agaacatcaa ggccttgatt    420
gagcatgaaa tgaagaacgg gatcattgcc aatcgaatcg tcctgggagg cttttcacag    480
ggcggggccc tgtccctcta cacggcctca actgcccca ncctctggtg gatctggcgt    540
tgactgtggc tgctctgca                                                 559

<210> SEQ ID NO 50
<211> LENGTH: 466
<212> TYPE: DNA
<213> ORGANISM: Homo sapiens
<220> FEATURE:
<221> NAME/KEY: misc_feature
<223> OTHER INFORMATION: Incyte ID No: 193790R6
<221> NAME/KEY: unsure
<222> LOCATION: 389
<223> OTHER INFORMATION: a, t, c, g, or other

<400> SEQUENCE: 50
tacggtttgg ggccctgacg gctgagaagc tccggtctgt tgtcacacct gccagggtcc      60
agttcaagac atacccgggt gtcatgcaca gctcctgtcc tcaggagatg gcagctgtga    120
aggaatttct tgagaagctg ctgcctcctg tctaactagt cgctggcccc agtgcagtac    180
cccagctcat gggggactca gcaagcaagc gtggcaccat cttggatctg agccggtcga    240
gcccctgtcc ccacccttcc tgacctgtcc ttttcccaca ggcctctggg ggcaggtggc    300
aaggcctggc cgggccttcc ttcctggcct tagccacctg gctctgtctg cagcaggggc    360
```

```
aggctgcttt cttatccatt tccctggang cgggcccccc tggcagagta ttggaggggc    420
tacaggcagc tggagaaagg ggccagccgc tgacccactc actcag                  466
```

<210> SEQ ID NO 51
<211> LENGTH: 385
<212> TYPE: DNA
<213> ORGANISM: Homo sapiens
<220> FEATURE:
<221> NAME/KEY: misc_feature
<223> OTHER INFORMATION: Incyte ID No: 1817542F6
<221> NAME/KEY: unsure
<222> LOCATION: 353, 363, 372
<223> OTHER INFORMATION: a, t, c, g, or other

<400> SEQUENCE: 51

```
agcaagcaag cgtggcacca tcttggatct gagccggtcg agccctgtc cccaccttc     60 ctgacctgtc cttttcccac aggcctctgg gggcaggtgg caaggcctgg ccgggccttc   120
cttcctggcc ttagccacct ggctctgtct gcagcagggg caggctgctt tcttatccat   180
ttccctggag gcgggccccc ctggcagcag tattggaggg gctacaggca gctgagaaa    240 ggggcccagc cgctgaccca ctcactcagg acctcactca ttagcccgt ttgggccccc    300 tcctgtgacc tcaggttttg gcccatgggg ccctcccagg ccctgcccc aantgattct    360 gcncagataa tnctgtctcc tgctc                                         385
```

<210> SEQ ID NO 52
<211> LENGTH: 320
<212> TYPE: DNA
<213> ORGANISM: Homo sapiens
<220> FEATURE:
<221> NAME/KEY: misc_feature
<223> OTHER INFORMATION: Incyte ID No: 1418115F1

<400> SEQUENCE: 52

```
gtgggctccc tgtccctggg caggagtgct ggtgaggagg tggagccttt tgagggggc     60 cttccctcag ctgtttcccc acactggggg gctgggccct gcctcccgt taccctcctt    120 ccctgcaggc ctggagcctg tagggctgga ctgaggttca ggtctccccc cagctgtctc   180
acccccactt tgtccccact ctagagcagg gaggcagtgg gggaggagtt gtgtctcgtc   240
ttctgtctcc atgtggtttt tgggtgtttt tcttgttgtg tcctggattc cgataaaatt   300
aaagaaattg cttcctcaaa                                               320
```

<210> SEQ ID NO 53
<211> LENGTH: 253
<212> TYPE: DNA
<213> ORGANISM: Homo sapiens
<220> FEATURE:
<221> NAME/KEY: misc_feature
<223> OTHER INFORMATION: Incyte ID No: 2886583H1

<400> SEQUENCE: 53

```
gcgcgatggc ggaggctgta ctgagggtcg cccggcggca gctgagccag cgcggcgggt    60
ctggagcccc catcctcctg cggcagatgt tcgagcctgt gagctgcacc ttcacgtacc   120
tgctgggtga cagagagtcc cgggaggcc ttctgatcga cccagtcctg gaaacagcgc    180
ctcgggatgc ccagctgatc aaggagctgg ggctgcggct gctctatgct gtgaataccc   240
actgccacgc gga                                                      253
```

<210> SEQ ID NO 54
<211> LENGTH: 458

```
<212> TYPE: DNA
<213> ORGANISM: Homo sapiens
<220> FEATURE:
<221> NAME/KEY: misc_feature
<223> OTHER INFORMATION: Incyte ID No: 1666224F6
<221> NAME/KEY: unsure
<222> LOCATION: 111
<223> OTHER INFORMATION: a, t, c, g, or other

<400> SEQUENCE: 54
gccgtagcgc ccggctcctg caggcgctcg gcctccgctc attcctgacc ccgcagtggg      60
cgcgatggca gaggctgtac tgagggtcgc ccggcggcag ctgagccagc ncggcgggtc     120
tggagccccc atcctcctgc ggcagatgtt cgagcctgtg agctgcacct tcacgtacct     180
gctgggtgac agagagtccc gggaggccgt tctgatcgac ccagtcctgg aaacagcgcc     240
tcgggatgcc cagctgatca aggagctggg gctgcggctg ctctatgctg tgaataccca     300
ctgccacgcg gaccacatta caggctcggg gctgctccgt tccctcctcc ctggctgcca     360
gtctgtcatc tcccgcctta gtggggccca ggctgactta cacattgagg atggagactc     420
catccgcttc gggcgttcgg ttggagacca gggccagc                             458

<210> SEQ ID NO 55
<211> LENGTH: 441
<212> TYPE: DNA
<213> ORGANISM: Homo sapiens
<220> FEATURE:
<221> NAME/KEY: misc_feature
<223> OTHER INFORMATION: Incyte ID No: 1223154R1
<221> NAME/KEY: unsure
<222> LOCATION: 362
<223> OTHER INFORMATION: a, t, c, g, or other

<400> SEQUENCE: 55
ggagatgccc tgttgatccg tgggtgtggg cggacagact tccagcaagg ctgtgccaag      60
accttgtacc actcggtcca tgaaaagatt tcacacttcc aggagactgt ctgatctaac     120
ctgctcacga ttaacatggg gtcacagtgt ccaccgtgga ggaggagagg actctgaacc     180
ctcggctcac cctcagctgt gaggagtttg tcaaaatcat gggcaacctg aacttgccta     240
aacctcagca gatagacttt gctgttccag ccaacatgcg ctgtggggtg cagacacccc     300
actgcctgat ctcacttctg tcagatgctc ccatccacta ttaatgcact aggtgggaag     360
anaaggcggc aatgcactg gaactctcct ttcccaacgg atttcctgga gctccctaaa      420
taaaaatttt tttaaacgtg a                                                441
```

HUMAN HYDROLASE-LIKE MOLECULES

This application is a continuation-in-part of U.S. Ser. No. 09/013,881, filed Feb. 6, 1998 now U.S. Pat. No. 6,137,964.

FIELD OF THE INVENTION

This invention relates to nucleic acid and amino acid sequences of human hydrolase-like molecules and to the use of these sequences in the diagnosis, or treatment of cell proliferation disorders, and autoimmune disorders.

BACKGROUND OF THE INVENTION

Hydrolysis is a common enzymatic mechanism. There are numerous enzymes whose catalytic mechanism involves breaking a covalent bond in a substrate by the addition of a molecule of water across the bond. The reaction involves a nucleophilic attack by the water molecule's oxygen atom on a target bond within the substrate and results in a splitting of the water molecule across the target bond, thereby breaking the bond and generating two product molecules. This general mechanism applies to a wide variety of enzymes including phosphatases, lysophospholipases, glyoxalases, and phosphodiesterases.

The protein phosphorylation/dephosphorylation cycle is one of the major regulatory mechanisms employed by eukaryotic cells to control cellular activities. During protein phosphorylalion, phosphate groups are transferred from adenosine triphosphate molecules to a protein by protein kinases. During protein dephosphorylation, phosphate groups are removed from a protein by protein phosphatases using a hydrolytic mechanism. In this manner, phosphatases are involved in the control of many cellular signaling events that regulate cell growth and differentiation, cell-to-cell contact, the cell cycle, and oncogenesis. Protein phosphatases may be characterized by amino acid residue specificity, for example, serine/threonine phosphatases, tyrosine phosphatases, or dual-specificity phosphatases. Dual-specificity phosphatases contain a conserved cysteine residue essential for catalytic activity. (Ishibashi et al. (1992) Proc Natl Acad Sci 89:12170–12174.)

Lysophospholipases (LPLs) are widely distributed enzymes that regulate intracellular lipids, and occur in numerous isoforms. These isoforms vary in molecular mass, the substrate metabolized, and the optimum pH required for activity. Small isoforms, approximately 15–30 kDa, function as hydrolases; large isoforms, those exceeding 60 kDa, function both as hydrolases and transacylases. A particular substrate for LPLs, lysophosphatidylcholine, causes lysis of cell membranes when it is formed or imported into a cell. LPLs are regulated by lipid factors including acylcarnitine, arachidonic acid, and phosphatidic acid. Thus, the activity of LPLs is regulated by signaling molecules important in numerous pathways including the inflammatory response.

The glyoxylase system consists of glyoxylase I, which catalyzes the formation of S-D-lactoylglutathione from methyglyoxal, a side product of triose-phosphate energy metabolism, and glyoxylase II, which hydrolyzes S-D-lactoylglutathione to D-lactic acid and reduced glutathione. Methyglyoxal levels are elevated during hyperglycemia and are likely due to increased triose-phosphate energy metabolism. Elevated levels of glyoxylase II activity have been found in human and in a rat model of non-insulin-dependent diabetes mellitus. The glyoxylase system has been implicated in the detoxification of bacterial toxins and in the control of cell proliferation and microtubule assembly. Elevated levels of S-D-lactoylglutathione, the substrate of glyoxylase II, induced growth arrest and toxicity in HL60 cells. Thus, the glyoxylase system, and glyoxylase II in particular, may be associated with cell proliferation and autoimmune disorders such as diabetes.

Sphingomyelin is a membrane phospholipid that is hydrolyzed to ceramide and phosphatidylcholine by the action of the phosphodiesterase, acid sphingomyelinase. Phosphatidylcholine is involved in numerous intracellular signaling pathways, while ceramide is an essential precursor for the generation of gangliosides, membrane lipids found in high concentration in neural tissue. Defective acid sphingomyelinase phosphodiesterase leads to a build-up of sphingomyelin molecules in lysosomes, resulting in Niemann-Pick disease.

Post-translation chemical modification of proteins, such as phosphorylation by protein kinase A, has been demonstrated to affect biochemical activity of enzymes (Krebs (1981) Curr Top Cell Regul 18:401–419). In a further example, protein kinase C a phosphorylates and activates the growth promoter Raf (Kolch et al. (1993) Nature 364: 249–252).

The discovery of new human hydrolase-like molecules and the polynucleotides encoding them satisfies a need in the art by providing new compositions which are useful in the diagnosis, or treatment of cell proliferation disorders and autoimmune disorders.

SUMMARY OF THE INVENTION

The invention features substantially purified polypeptides, human hydrolase-like molecules, referred to collectively as "HHLM" and individually as "HHLM 1–8". In one aspect, the invention provides a substantially purified polypeptide comprising an amino acid sequence selected from the group consisting of SEQ ID NOs:1–8 or portions or fragments thereof.

The invention further provides a substantially purified variant having at least 81% amino acid identity to the amino acid sequences of SEQ ID NOs:11–8 or fragments thereof. The invention also provides an antigenic epitope selected from SEQ ID NOs:1–8, an oligopeptide selected from of SEQ ID NOs:1–8, and a biologically active portion selected from SEQ ID NOs:1–8. The invention also includes an isolated and purified polynucleotide variant having at least 90% polynucleotide sequence identity to the polynucleotide encoding the polypeptide comprising an amino acid sequence selected from the group consisting of SEQ ID NOs:1–8 or fragments thereof.

Additionally, the invention provides an isolated and purified polynucleotide which hybridizes under stringent conditions to the polynucleotide encoding the polypeptide comprising an amino acid sequence selected from the group consisting of SEQ ID NOs:1–8 or fragments thereof, as well as an isolated and purified polynucleotide having a sequence which is complementary to the polynucleotide encoding the polypeptide comprising the amino acid sequence selected from the group consisting of SEQ ID NOs:1–8 or fragments thereof. The invention also provides a purified polypeptide of an amino acid sequence encoded by a polynucleotide selected from SEQ ID NOs:17–55.

The invention also provides an isolated and purified polynucleotide comprising a polynucleotide sequence selected from the group consisting of SEQ ID NOs:9–16 or fragments thereof. The invention further provides an isolated and purified polynucleotide variant having at least 90% polynucleotide sequence identity to the polynucleotide sequence comprising a polynucleotide sequence selected from the group consisting of SEQ ID NOs:9–16 or fragments thereof, as well as an isolated and purified polynucleotide having a sequence which is complementary to the polynucleotide comprising a polynucleotide sequence selected from the group consisting of SEQ ID NOs:9–16 or fragments thereof The invention also provides an isolated and purified polynucleotide comprising a polynucleotide sequence selected from the group consisting of SEQ ID NOs:17–55 or fragments thereof. The invention further provides an isolated and purified polynucleotide variant having at least 90% polynucleotide sequence identity to the polynucleotide sequence comprising a polynucleotide sequence selected from the group consisting of SEQ ID NOs:17–55 or fragments thereof, as well as an isolated and purified polynucleotide having a sequence which is complementary to the polynucleotide comprising a polynucleotide sequence selected from the group consisting of SEQ ID NOs:17–55 or fragments thereof The invention further provides an expression vector containing at least a fragment of the polynucleotide encoding the polypeptide comprising an amino acid sequence selected from the group consisting of SEQ ID NOs:1–8 or fragments thereof. In another aspect, the expression vector is contained within a host cell.

The invention also provides a method for producing a polypeptide comprising the amino acid sequence of SEQ ID NOs:1–8 or fragments thereof, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified HHLM having the amino acid sequence of SEQ ID NOs:1–8 or fragments thereof in conjunction with a suitable pharmaceutical carrier.

The invention further includes a purified antibody which binds to a polypeptide comprising the amino acid sequence of SEQ ID NOs:1–8 or fragments thereof, as well as a purified agonist and a purified antagonist to the polypeptide.

The invention also provides a method for treating or preventing a cell proliferation disorder, the method comprising administering to a subject in need of such treatment an effective amount of an antagonist of the polypeptide having an amino acid sequence of SEQ ID NOs:1–8 or fragments thereof.

The invention also provides a method for treating or preventing an autoimmune disorder, the method comprising administering to a subject in need of such treatment an effective amount of an antagonist of the polypeptide having an amino acid sequence of SEQ ID NOs:1–8 or fragments thereof.

The invention also provides a method for detecting a polynucleotide encoding the polypeptide comprising the amino acid sequence SEQ ID NOs:1–8 or fragments thereof in a biological sample containing nucleic acids, the method comprising the steps of: (a) hybridizing the complement of the polynucleotide sequence encoding the polypeptide comprising SEQ ID NOs:1–8 or fragments thereof to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

The invention further provides a method of using a polypeptide to screen a plurality of molecules or compounds to identify a ligand which specifically binds the polypeptide. In one aspect, the molecules or compounds are selected from DNA molecules, RNA molecules, peptide nucleic acids, peptides, proteins, mimetics, agonists, antagonists, antibodies, immunoglobulins, inhibitors, and drugs.

The invention further provides a method of using a polypeptide to screen subject sample for antibodies which specifically bind the polypeptide.

The invention further provides a method of using a polypeptide to prepare and purify antibodies which specifically bind the polypeptide.

BRIEF DESCRIPTION OF THE FIGURES

FIG. 1 demonstrates the conserved chemical and structural similarities among the sequences of HHLM 1 (094168; SEQ ID NO:1) and HHLM 6 (2011230; SEQ ID NO:6), respectively. The alignment was produced using the MEGALIGN program of LASERGENE software (DNASTAR, Madison Wis.).

FIGS. 2A and 2B demonstrate the conserved chemical and structural similarities among the sequences of HHLM 3 (507537; SEQ ID NO:3) and HHLM 4 (971204; SEQ ID NO:4), respectively. The alignment was produced using the MEGALIGN program of LASERGENE software (DNASTAR).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"HHLM" refers to the amino acid sequences of substantially purified HHLM obtained from any species, particularly a mammalian species, including bovine, ovine, porcine, murine, equine, and preferably the human species, from any source, whether natural, synthetic, semi-synthetic, or recombinant.

"cDNA" refers to an isolated polynucleotide, nucleic acid molecule, or any fragment or complement thereof. It may have originated recombinantly or synthetically, be double-stranded or single-stranded, represent coding and/or non-coding sequence, an exon with or without an intron from a genomic DNA molecule.

The phrase "cDNA encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Evol 36: 290–300; Altschul et al. (1990) J Mol Biol 215:403–410) which provides identity within the conserved region.

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by the absence, presence, or at least two-fold changes in the amount of transcribed messenger RNA or translated protein in a sample.

"Disorder" refers to conditions, diseases or syndromes in which the cDNAs and protname are differentially expressed.

"Fragment" refers to a chain of consecutive nucleotides from about 200 to about 700 base pairs in length. Fragments may be used in PCR or hybridization technologies to identify related nucleic acid molecules and in binding assays to screen for a ligand. Nucleic acids and their ligands identified in this manner are useful as therapeutics to regulate replication, transcription or translation.

An "allele" or an "allelic sequence" is an alternative form of the gene encoding HHLM. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HHLM include those sequences with deletions, insertions, or substitutions of different nucleotides, resulting in a polynucleotide the same HHLM or a polypeptide with at least one functional characteristic of HHLM. Included within this definition are polymorphisms which may or may not be readily detectable using a particular oligonucleotide probe of the polynucleotide encoding HHLM, and improper or unexpected hybridization to alleles, with a locus other than the normal chromosomal locus for the polynucleotide sequence encoding HHLM. The encoded protein may also be "altered," and may contain deletions, insertions, or substitutions of amino acid residues which produce a silent change and result in a functionally equivalent HHLM. Deliberate amino acid substitutions may be made on the basis of similarity in polarity, charge, solubility, hydrophobicity, hydrophilicity, and/or the amphipathic nature of the residues, as long as the biological or immunological activity of HHLM is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

"Amino acid" or "amino acid sequence" refer to an oligopeptide, peptide, polypeptide, or protein sequence, or a portion or a fragment of any of these, and to naturally occurring or synthetic molecules. In this context, "fragments", "immunogenic fragments", or "antigenic fragments" refer to fragments of HHLM which are preferably about 5 to about 15 amino acids in length and which retain some biological activity or immunological activity of HHLM. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR, Madison Wis.). An "oligopeptide" is an amino acid sequence from about five residues to about 15 residues that is used as part of a fusion protein to produce an antibody.

"Amplification" relates to the production of additional copies of a nucleic acid sequence. Amplification is generally carried out using polymerase chain reaction (PCR) technologies well known in the art. (See, e.g., Dieffenbach and Dveksler (1995) *PCR Primer, a Laboratory Manual*, Cold Spring Harbor Press, Plainview N.Y., pp. 1–5.)

"Antibody" refers to intact molecules as well as to fragments thereof, such as Fa, F(ab')$_2$, and Fv fragments, which are capable of binding the epitopic determinant. Antibodies that bind HHLM polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

"Antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

"Antisense" refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

"Biologically active" refers to a protein having structural, regulatory, or biochemical functions of a naturally occurring molecule. Likewise, "immunologically active" refers to the capability of the natural, recombinant, or synthetic HHLM, or of any oligopeptide thereof, to induce a specific immune response in appropriate animals or cells and to bind with specific antibodies.

"Complementary" or "complementarity" refer to the natural binding of polynucleotides under permissive salt and temperature conditions by base pairing. For example, the sequence 5'-A-G-T-C-3' base pairs with 3'-T-C-A-G-5'. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules. The complement of a cDNA of the Sequence Listing refers to a nucleic acid molecule which is completely complementary over its full length and which will hybridize to the cDNA or an mRNA under conditions of high stringency.

A "composition comprising a given polynucleotide sequence" or a "composition comprising a given amino acid sequence" refer broadly to any composition containing the given polynucleotide or amino acid sequence. The composition may comprise a dry formulation, an aqueous solution, or a sterile composition. Compositions comprising polynucleotide sequences encoding HHLM or fragments of HHLM may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (PE Biosystems, Foster City Calif.) in the 5' and/or the 3' direction, and resequenced, or which has been assembled from the overlapping sequences of more than one Incyte Clone using a computer program for fragment assembly, such as the GELVIEW fragment assembly system (Genetics Computer Group, Madison Wis.). Some sequences have been both extended and assembled to produce the consensus sequence .

The term "correlates with expression of a polynucleotide" indicates that the detection of the presence of nucleic acids, the same or related to a nucleic acid sequence encoding HHLM, by northern analysis is indicative of the presence of nucleic acids encoding HHLM in a sample, and thereby correlates with expression of the transcript from the polynucleotide encoding HHLM.

"Deletion" refers to a change in the amino acid or nucleotide sequence that results in the absence of one or more amino acid residues or nucleotides.

"Derivative" refers to the chemical modification of HHLM, of a polynucleotide sequence encoding HHLM, or of a polynucleotide sequence complementary to a polynucleotide sequence encoding HHLM. Chemical modifications of a polynucleotide sequence can include, for example, replacement of hydrogen by an alkyl, acyl, or amino group.

A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

"Homology" refers to a degree of complementarity. There may be partial homology or complete homology. A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

"Human artificial chromosomes" are linear microchromosomes which may contain DNA sequences of about 6 kbp to 10 Mbp in size, and which contain all of the elements required for stable nutotic chromosome segregation and maintenance. (See, e.g., Harrington et al. (1997) Nat Genet 15:345–355.)

"Humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing. "Hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition" refers to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

"Microarray" refers to an arrangement of distinct polynucleotides or oligonucleotides arrayed on a substrate.

"Modulate" refers to a change in the activity of HHLM. For example, modulation may cause an increase or a decrease in protein activity, binding characteristics, or any other biological, functional, or immunological properties of HHLM.

"Polynucleotide" refers to an oligonucleotide, nucleic acid sequence, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are from about 60 nucleotides in length to about 10,000 nucleotides in length.

"Operably associated" or "operably linked" refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

"Oligonucleotide" refers to a nucleic acid molecule of at least about 6 nucleotides to about 60 nucleotides, which can be used in PCR amplification or in a hybridization assay or microarray and is substantially equivalent to the terms "amplimer", "primer", "oligomer", and "probe", as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen et al. (1993) Anticancer Drug Des 8:53–63.)

"Portion" refers to any part of a protein used for any purpose; but especially, to an epitope for the screening of ligands or for the production of antibodies.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleic acid sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acids are completely complementary. In some membrane-based hybridizations, preferably 35% or most preferably 50% formamide can be added to the hybridization solution to reduce the temperature at which hybridization is performed, and background signals can be reduced by the use of other detergents such as Sarkosyl or Triton X-100 and a blocking agent such as denatured salmon sperm DNA. Selection of components and conditions for hybridization are well known to those skilled in the art and are reviewed in Ausubel (supra and Sambrook et al. (1989) *Molecular Cloning, A Laboratory Manual*, Cold Spring Harbor Press, Plainview N.Y.

"Substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. "Transformed" cells includes stably transformed cells in which the inserted DNA is capable of replication either as an autonomously replicating plasmid or as part of the host chromosome, as well as transiently transformed cells which express the inserted DNA or RNA for limited periods of time.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid. Guidance in determining which amino acid residues may be substituted, inserted, or deleted without abolishing biological or immunological activity may be found using computer programs well known in the art, for example, LASERGENE software (DNASTAR). The encoded protein may also contain deletions, insertions, or substitutions of amino acid residues which produce a silent change and result in a functionally equivalent HHLM. Deliberate amino acid substitutions may be made on the basis of similarity in polarity, charge, solubility, hydrophobicity, hydrophilicity, and/or the amphipathic nature of the residues, as long as the biological or immunological activity of HHLM is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine. A variant of a protein may have a biologically active region and have at least 75% amino acid similarity over at least thirty contiguous amino acid residues of the region of activity.

THE INVENTION

The invention is based on the discovery of new human hydrolase-like molecules (HHLM), the polynucleotides encoding HHLM, and the use of these compositions for the diagnosis, or treatment of cell proliferation disorders and autoimmune disorders. Table 1 shows the sequence identification numbers, Incyte Clone identification number, and cDNA library for each of the human hydrolase-like molecules disclosed herein.

TABLE 1

| Protein | Nucleotide | Clone ID | Library |
| --- | --- | --- | --- |
| SEQ ID NO:1 | SEQ ID NO:9 | 094168 | PITUNOT1 |
| SEQ ID NO:2 | SEQ ID NO:10 | 195647 | KIDNNOT02 |
| SEQ ID NO:3 | SEQ ID NO:11 | 507537 | TMLR3DT02 |
| SEQ ID NO:4 | SEQ ID NO:12 | 971204 | MUSCNOT02 |
| SEQ ID NO:5 | SEQ ID NO:13 | 1376382 | LUNGNOT10 |
| SEQ ID NO:6 | SEQ ID NO:14 | 2011230 | TESTNOT03 |
| SEQ ID NO:7 | SEQ ID NO:15 | 2768301 | COLANOT02 |
| SEQ ID NO:8 | SEQ ID NO:16 | 2886583 | SINJNOT02 |

Nucleic acids encoding the HHLM 1 of the present invention were first identified in Incyte Clone 094168 from the human pituitary gland cDNA library (PITUNOT01) using a computer search for amino acid sequence alignments. A consensus sequence, SEQ ID NO:9, was derived from the following overlapping and/or extended nucleic acid sequences: Incyte Clones 094168H1 (PITUNOT01), 2470694F6 (THPINOT03), 3595859H1 (FIBPNOT01), 1864296F6 and 1864296T6 (PROSNOT19), 1622192F6 (BRAITUT13), 1695044F6 (COLNNOT23), and 1431642T1 (BEPINON01), SEQ ID NOs:17–24, respectively. The fragment of SEQ ID NO:9 from about nucleotide 120 to about nucleotide 180 is useful as a hybridization probe. Northern analysis shows the expression of this sequence in neural, reproductive and cardiovascular tissue libraries, at least 61% of which are immortalized or cancerous. Of particular note is the expression of HHLM 1 in ovarian and breast cancer.

In one embodiment, the invention encompasses a polypeptide comprising the amino acid sequence of SEQ ID NO:1. HHLM 1 is 259 amino acids in length and has a potential glycosylation site at N47, seven potential casein kinase II phosphorylation sites at T48, S52, S68, S81, T164, T1 92, an S231. In addition HHLM 1 has two potential protein kinase C phosphorylation sites at T48 and T225. HHLM 1 has chemical and structural homology with *C. elegans* 4-nitrophenylphosphatase (PPNase; g1938421). In particular, HHLM 1 and PPNase share 51% identity, as well as sharing four potential phosphorylation sites and a potential glycosylation site. The portion of SEQ ID NO:1 from about residue G217 to about residue E233 is useful as a fragment with biological activity. The portion of SEQ ID NO:1 from about residue A199 to about residue Q214 is useful as an oligopeptide. The portion of SEQ ID NO:1 from about residue Y148 to about residue A156 is useful as an antigenic epitope.

Nucleic acids encoding the HHLM 2 of the present invention were first identified in Incyte Clone 195647 from the human kidney cDNA library (KIDNNOT02) using a computer search for amino acid sequence alignments. A consensus sequence, SEQ ID NO:10, was derived from the following overlapping and/or extended nucleic acid sequences: Incyte Clones 195647R1 (KIDNNOT02), 1795063H1 (PROSTUT05), 1813266F6 (PROSTUT12), and 728148X27 (SYNOOAT01), SEQ ID NOs:25–28, respectively. The fragment of SEQ ID NO:10 from about nucleotide 74 to about nucleotide 134 is useful as a hybridization probe. Northern analysis shows the expression of this sequence in reproductive, neural, hematopoietic, and gastrointestinal tissue libraries, at least 43% of which are immortalized or cancerous and at least 20% of which involve inflammation and the immune response. Of particular note is the expression of HHLM 2 in brain and prostate tumors.

In one embodiment, the invention encompasses a polypeptide comprising the amino acid sequence of SEQ ID NO:2. HHLM 2 is 392 amino acids in length, and has a protein phosphatase 2C signature sequence from Y147 through G155, as well as a potential glycosarinoglycan attachment site at S40. In addition, HHLM 2 has two potential glycosylation site at N87 and N382, two potential cAMP- and cGMP-dependent protein kinase phosphorylation sites at T81 and T82, twelve potential casein kinase II phosphorylation sites at S36, S55, T81, T82, T198, T263, S292, S305, T315, T333, five potential protein kinase C phosphorylation sites at S13, T186, T194, S208, and S248, and two potential tyrosine kinase phosphorylation sites at Y298 and Y363. HHLM 2 has chemical and structural homology with human phosphatase 2C motif (PP2C; g2114221). In particular, HHLM 2 and PP2C share 26% identity and are completely identical throughout the protein phosphatase 2C signature sequence, residues Y147 through G155 of SEQ ID NO:2. HHLM 2 and PP2C also share two potential phosphorylation sites and a potential glycosaminoglycan attachment site. The portion of SEQ ID NO:2 from about residue Y147 to about residue A163 is useful as a fragment with biological activity. The portion of SEQ ID NO:2 from about residue K185 to about residue E201 is useful as an oligopeptide. The portion of SEQ ID NO:2 from about residue K71 to about residue L92 is useful as an antigenic epitope.

Nucleic acids encoding the HHLM 3 of the present invention were first identified in Incyte Clone 507537 from the human blood mononuclear cell cDNA library (TMLR3DT02) using a computer search for amino acid sequence alignments. A consensus sequence, SEQ ID NO:11, was derived from the following overlapping and/or extended nucleic acid sequences: Incyte Clones 507537X14 (TMLR3DT02), 868893H1 (LUNGAST01), 2272231R6 (PROSNON01), 2379239F7 (ISLTNOT01), 1397852F1 (BRAITUT08), SEQ ID NOs:29–33, respectively. The fragment of SEQ ID NO:11 from about nucleotide 72 to about nucleotide 132 is useful as a hybridization probe. Northern analysis shows the expression of this sequence in hematopoietic and immune, reproductive, and cardiovascular tissue libraries, at least 49% of which are immortalized or cancerous and at least 37% of which involve inflammation and the immune response. Of particular note is the expression of HHLM 3 in lymphocytes and a T-cell line.

In one embodiment, the invention encompasses a polypeptide comprising the amino acid sequence of SEQ ID NO:3. HHLM 3 is 353 amino acids in length and has a potential cAMP- and cGMP-dependent protein kinase phosphorylation site at T265, two potential casein kinase II phosphorylation sites at S105 and S246, five potential protein kinase C phosphorylation sites at S78, T201, T272, S307, and T350, and a microbodies C-terminal targeting signal at L35 1. HHLM 3 has chemical and structural homology with S. cerevisiae phosphatase (ScPPase; g172168). In particular, HHLM 3 and ScPPase share 30% identity, including a potential protein kinase C phosphorylation site. The portion of SEQ ID NO:3 from about residue V124 to about residue I138 is useful as a fragment with biological activity. The portion of SEQ ID NO:3 from about residue T101 to about residue I114 is useful as an oligopeptide. The portion of SEQ ID NO:3 from about residue K199 to about residue Q212 is useful as an antigenic epitope.

Nucleic acids encoding the HHLM 4 of the present invention were first identified in Incyte Clone 971204 from the human muscle tissue cDNA library (MUSCNOT02) using a computer search for amino acid sequence alignments. A consensus sequence, SEQ ID NO:12, was derived from the following overlapping and/or extended nucleic acid sequences: Incyte Clones 971204X37 (MUSCNOT02), 2822470F6 (ADRETUT06), and shotgun sequences STEQ00223R1 and STEQ02003R1, SEQ ID NOs:34–37, respectively. The fragment of SEQ ID NO:12 from about nucleotide 412 to about nucleotide 472 is useful as a hybridization probe. Northern analysis shows the expression of this sequence in cardiovascular, neural, and reproductive tissue libraries, at least 40% of which are immortalized or cancerous. Of particular note is the expression of HHLM 4 in ovarian cancers.

In one embodiment, the invention encompasses a polypeptide comprising the amino acid sequence of SEQ ID NO:4. HHLM 4 is 207 amino acids in length and has a tyrosine protein phosphatase active site signature sequence from V146 through LI58. In addition, HHLM 4 has a potential glycosylation site at N93, three potential casein kinase II phosphorylation sites at T31, T128, and T170, and two potential protein kinase C phosphorylation sites at S21 and T54. HHLM 4 has chemical and structural homology with human dual-specificity protein phosphatase (tyrosinelserine) (HPPase; g181840). In particular, HHLM 4 and HPPase share 37% identity, including over 90% similarity in the tyrosine specific protein phosphatases active site signature sequence and the conserved cysteine residue essential for catalytic activity. The portion of SEQ ID NO:4 from about residue L145 to about residue L160 is useful as a fragment with biological activity. The portion of SEQ ID NO:4 from about residue F120 to about residue 1133 is useful as an oligopeptide. The portion of SEQ ID NO:4 from about residue M76 to about residue G87 is useful as an antigenic epitope. Nucleic acids encoding the HHLM 5 of the present invention were first identified in Incyte Clone 1376382 from the human lung tissue cDNA library (LUNGNOT10) using a computer search for amino acid sequence alignments. A consensus sequence, SEQ ID NO:13, was derived from the following overlapping and/or extended nucleic acid sequences: Incyte Clone 1376382F6 (LUNGNOT10) and shotgun sequences SAEA03372R1, SAEA02307F1, SAEA02307R1, and SAEA02991R1, SEQ ID NOs:38–42, respectively. The fragment of SEQ ID NO:13 from about nucleotide 69 to about nucleotide 128 is useful as a hybridization probe. Northern analysis shows the expression of this sequence in reproductive, gastrointestinal, and hematopoietic and immune tissue libraries, at least 55% of which are immortalized or cancerous and at least 26% of which involve inflammation and the immune response. Of particular note is the expression of HHLM 5 in tumors of the prostate, uterus, testicle, and breast. In one embodiment, the invention encompasses a polypeptide comprising the amino acid sequence of SEQ ID NO:5. HHLM 5 is 453 amino acids in length and has seven potential glycosylation sites at N69, N131, N222, N238, N263, N356, and N437. In addition, HHLM 5 has a potential and cGMP-dependent protein kinase phosphorylation site at S308, six potential casein kinase II phosphorylation sites at S90, S98, T294, S324, T396 and S439, a potential glycosaminoglycan attachment site at S19, seven potential protein kinase C phosphorylation sites at S64, T164, T186, S194, T294, S303, and T423, and a potential tyrosine kinase phosphorylation site at Y353. HHLM 5 has chemical and structural homology with mouse acid sphingomyelinase-like phosphodiesterase (MASP; g1552350). In particular, HHLM 5 and MASP share 79% identity, including seven potential phosphorylation sites and five potential glycosylation sites. The portion of SEQ ID NO:5 from about residue F290 to about residue K305 is useful as a fragment with biological activity. The portion of SEQ ID NO:5 from about residue 11 84 to about residue N200 is useful as an oligopeptide. The portion of SEQ ID NO:5 from about residue Q339 to about residue Q352 is useful as an antigenic epitope.

Nucleic acids encoding the HHLM 6 of the present invention were first identified in Incyte Clone 2011230 from the human testicular tissue cDNA library (TESTNOT03) using a computer search for amino acid sequence alignments. A consensus sequence, SEQ ID NO:14, was derived from the following overlapping and/or extended nucleic acid sequences: Incyte Clones 2011230R6 (TESTNOT03), 2855308H1 (CONNNOT02), 1706605F6 (DUODNOT02), and 1482295F6 and 1481157T6 (CORPNOT02), SEQ ID NOs:43–47, respectively. The fragment of SEQ ID NO:14 from about nucleotide 19 to about nucleotide 72 is useful as a hybridization probe. Northern analysis shows the expression of this sequence in neural, reproductive, and gastrointestinal tissue libraries, at least 47% of which are immortalized or cancerous and at least 24% of which involve inflammation and the immune response. Of particular note is the expression of HHLM 6 in tumors of the brain and ganglion.

In one embodiment, the invention encompasses a polypeptide comprising the amino acid sequence of SEQ ID NO:6. HHLM 6 is 270 amino acids in length and has a potential amidation site at W4, a potential glycosylation site at N55, and a glycosaminoglycan attachment site at S25. In addition, HHLM 6 has three potential casein kinase II phosphorylation sites at S60, S76, and S108, and two potential protein kinase C phosphorylation sites at S57 and T235. HHLM 6 has chemical and structural homology with C. elegans 4-nitrophenylphosphatase (PPNase; g1938421). In particular, HHLM 6 and PPNase share 35% identity, including two potential phosphorylation sites and a potential glycosylation site. The portion of SEQ ID NO:6 from about residue G227 to about residue E243 is useful as a fragment with biological activity. The portion of SEQ ID NO:6 from about residue A209 to about residue Q224 is useful as an oligopeptide. The portion of SEQ ID NO:6 from about residue K155 to about residue L167 is useful as an antigenic epitope.

Nucleic acids encoding the HHLM 7 of the present invention were first identified in Incyte Clone 2768301 from the human colon tissue cDNA library (COLANOT02) using a computer search for amino acid sequence alignments. A consensus sequence, SEQ ID NO:15, was derived from the following overlapping and/or extended nucleic acid sequences: Incyte Clones 2768301 H1 (COLANOT02), 1582462F6 (DUODNOT01), 193790R6 (KIDNNOT02), 1817542F6 (PROSNOT20), and 1418115F1 (KIDNNOT09), SEQ ID NOs:48–52, respectively. The fragment of SEQ ID NO:15 from about nucleotide 113 to about nucleotide 166 is useful as a hybridization probe. Northern analysis shows the expression of this sequence in reproductive, gastrointestinal, and developmental tissue libraries, at least 60% of which are immortalized or cancerous and at least 22% of which involve the inflammatory response. Of particular note is the expression of HHLM 7 in tumors of the breast and prostate.

In one embodiment, the invention encompasses a polypeptide comprising the amino acid sequence of SEQ ID NO:7. HHLM 7 is 231 amino acids in length. HHLM 7 has a potential glycosylation site at N160, four potential casein kinase II phosphorylation sites at S18, S39, S74, and S162, and two potential protein kinase C phosphorylation sites at T46 and S162. HHLM 7 has chemical and structural homology with mouse lysophospholipase I (MLP; g1864159). In particular, HHLM 7 and MLP share 65% identity. The portion of SEQ ID NO:7 from about residue H137 to about residue R153 is useful as a fragment with biological activity. The portion of SEQ ID NO:7 from about residue A158 to about residue H172 is useful as an oligopeptide. The portion of SEQ ID NO:7 from about residue P84 to about residue N98 is useful as an antigenic epitope.

Nucleic acids encoding the HHLM 8 of the present invention were first identified in Incyte Clone 2886583 from the human jejunum tissue cDNA library (SINJNOT02) using a computer search for amino acid sequence alignments. A consensus sequence, SEQ ID NO:1 6, was derived from the following overlapping and/or extended nucleic acid sequences: Incyte Clones 2886583H1 (SINJNOT02), 1666224F6 (BRSTNOT09), and 1223154R1 (COLNTUT02), SEQ ID NOs:53–55, respectively. The fragment of SEQ ID NO:16 from about nucleotide 66 to about nucleotide 123 is useful as a hybridization probe. Northern analysis shows the expression of this sequence in gastrointestinal and reproductive tissue libraries, at least 69% of which are immortalized or cancerous and at least 26% of which involve inflammation and the immune response. Of particular note is the expression of HHLM in tumors of the prostate and colon.

In one embodiment, the invention encompasses a polypeptide comprising the amino acid sequence of SEQ ID NO:8. HHLM is 254 amino acids in length and has four potential casein kinase II phosphorylation sites at S177, S203, T204, and S218, and two potential protein kinase C phosphorylation sites at S14 and S119. HHLM 8 has chemical and structural homology with A. thaliana glyoxylase II (AGLX; g1644427). In particular, HHLM and AGLX share 57% identity, including a potential phosphorylation site. The portion of SEQ ID NO:8 from about residue D188 to about residue T201 is useful as a fragment with biological activity. The portion of SEQ ID NO:8 from about residue G169 to about residue 1182 is useful as an oligopeptide. The portion of SEQ ID NO:8 from about residue G41 to about residue 151 is useful as an antigenic epitope.

As shown in FIG. 1, HHLM 1 has chemical and structural homology with HHLM 6. In particular, HHLM 1 and HHLM 6 share 41% identity, including two potential phosphorylation sites, and a potential glycosylation site. In addition, HHLM 1 and HHLM 6 share a conserved region between A199-E233 and A209-E243, respectively. The conserved regions of HHLM 1 and HHLM 6 share 66% identity (77% similarity with conservative residue substitutions) and include a potential protein kinase C phosphorylation site at T225 and T235, respectively.

As shown in FIGS. 2A and 2B, HHLM 3 has chemical and structural homology with HHLM 4. In particular, HHLM 3 and HHLM 4 share 18% identity, including a conserved region between L125-I138 and L145-L158, respectively, and a potential casein kinase II phosphorylation site. The conserved regions of HHLM 3 and HHLM 4 share 64% identity (79% similarity with conservative residue substitutions) and includes a cysteine residue potentially essential for catalytic activity.

The invention also encompasses HHLM variants. A preferred HHLM variant is one which has at least about 80%, more preferably at least about 90%, and most preferably at least about 95% amino acid sequence identity to the HHLM amino acid sequence, and which contains at least one functional or structural characteristic of HHLM.

The invention also encompasses polynucleotides which encode HHLM. In a particular embodiment, the invention encompasses a polynucleotide sequence comprising a polynucleotide sequence selected from the group consisting of SEQ ID NOs:9–16, which encode HHLM.

The invention also encompasses polynucleotides which encode a portion of HHLM. In a particular embodiment, the invention encompasses a polynucleotide sequence comprising a polynucleotide sequence selected from the group consisting of SEQ ID NOs:17–55, which encode a portion of HHLM.

The invention also encompasses a variant of a polynucleotide sequence encoding HHLM. In particular, such a variant polynucleotide sequence will have at least about 80%, more preferably at least about 90%, and most preferably at least about 95% polynucleotide sequence identity to the polynucleotide sequence encoding HHLM. Any one of the polynucleotide variants can encode an amino acid sequence which contains at least one functional or structural characteristic of HHLM.

It will be appreciated by those skilled in the art that as a result of the degeneracy of the genetic code, a multitude of polynucleotide sequences encoding HHLM, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HHLM, and all such variations are to be considered as being specifically disclosed.

Although nucleotide sequences which encode HHLM and its variants are preferably capable of hybridizing to the nucleotide sequence of the naturally occurring HHLM under appropriately selected conditions of stringency, it may be advantageous to produce nucleotide sequences encoding HHLM or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HHLM and its derivatives without altering the encoded amino acid sequences include the production of RNA transcripts having more desirable properties, such as a greater half-life, than transcripts produced from the naturally occurring sequence.

The invention also encompasses production of DNA sequences which encode HHLM and HHLM derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HHLM or any fragment thereof.

Also encompassed by the invention are polynucleotide sequences that are capable of hybridizing to the claimed polynucleotide sequences, and, in particular, to those shown in SEQ ID NOs:9–16 or fragments thereof under various conditions of stringency. The invention also encompasses polynucleotide sequences that are capable of hybridizing to the claimed polynucleotide sequences, and, in particular, to those shown in SEQ ID NOs:17–55 or fragments thereof under various conditions of stringency. (See, e.g., Wahl and Berger (1987) Methods Enzymol. 152:399–407; and Kimmel (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase 1, T7 SEQUENASE DNA polymerase, Taq DNA polymerase, THERMOSEQUENASE DNA polymerase (Amersham Pharnacia Biotech (APB), Piscataway N.J.), or combinations of polymerases and proofreading exonucleases such as those found in the ELONGASE amplification system (Life Technologies, Gaithersburg Md.). Preferably, the process is automated with machines such as the MICROLAB 2200 system (Hamilton, Reno Nev.), DNA ENGINE thermal cycler (MJ Research, Watertown Mass.) and ABI CATALYST thermal cycler and the ABI PRISM 373 and 377 sequencing systems (PE Biosystems).

The nucleic acid sequences encoding HHLM may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar (1993) PCR Methods Applic 2:318–322.) In particular, genomic DNA is first amplified in the presence of a primer which is complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia et al. (1988) Nucleic Acids Res 16:8186.) The primers may be designed using commercially available software such as OLIGO 4.06 primer analysis software (National Biosciences, Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom et al. (199 1) PCR Methods Applic 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker et al. (1991) Nucleic Acids Res 19:3055–3060.) Additionally, one may use PCR and nested primers to walk genomic DNA. This process avoids the need to screen libraries and is useful in finding intron/exon junctions. When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR analysis software, PE Biosystems), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HHLM may be used in recombinant DNA molecules to direct expression of HHLM, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HHLM.

As will be understood by those of skill in the art, it may be advantageous to produce HHLM-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HHLM-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HHLM may be ligated to a heterologous sequence to encode a fusion protein. For example, to screen peptide libraries for inhibitors of HHLM activity, it may be useful to encode a chimeric HHLM protein that can be recognized by a commercially available antibody. A fusion protein may also be engineered to contain a cleavage site located between the HHLM-encoding sequence and the heterologous protein sequence, so that HHLM may be cleaved and purified away from the heterologous moiety.

In another embodiment, sequences encoding HHLM may be synthesized, in whole or in part, using chemical methods well known in the art. (See, e.g., Caruthers et al. (1980) Nucleic Acids Symp Ser (7) 215–223; and Horn et al. (1980) Nucleic Acids Symp Ser (7) 225–232.) Alternatively, the prote itself may be produced using chemical methods to synthesize the amino acid sequence of HHLM, or a fragment thereof. For example, peptide synthesis can be performed using various solid-phase techniques. (See, e.g., Roberge et al. (1995) Science 269:202–204.) Automated synthesis may be achieved using the ABI 431A peptide synthesizer (PE Biosystems). Additionally, the amino acid sequence of HHLM, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez and Regnier (1990) Methods Enzymol 182:392421.) The composition of the synthetic peptides may be confirmed by amino acid analysis or by sequencing. (See, e.g., Creighton (1 983) *Proteins, Structures and Molecular Properties*, WH Freeman and Co., New York N.Y.)

In order to express a biologically active HHLM, the nucleotide sequences encoding HHLM or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HHLM and appropriate transcriptional and translational control elements. These methods include in vitro recombinant DNA techniques, synthetic techniques, and in vivo genetic recombination. (See, e.g., Sambrook et al. (1989) *Molecular Cloning, A Laboratory Manual*, Cold Spring Harbor Press, Plainview N.Y., ch. 4, 8, and 16–17; and Ausubel et al. (1995, and periodic supplements) *Current Protocols in Molecular Biology*, John Wiley & Sons, New York N.Y., ch. 9, 13, and 16.)

A variety of expression vector/host systems may be utilized to contain and express sequences encoding HHLM. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HHLM which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the BLUESCRIPT phagemid (Stratagene, La Jolla Calif.) or PSPORT1 plasmid (Life Technologies), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HHLM, vectors based on SV40 or EBV may be used with an appropriate selectable marker.

In bacterial systems, a number of expression vectors may be selected depending upon the use intended for HHLM. For example, when large quantities of HHLM are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding HHLM may be ligated into the vector in frame with sequences for the amino-terminal Met and the subsequent 7 residues of β-galactosidase so that a hybrid protein is produced, and pIN vectors. (See, e.g., Van Heeke and Schuster (1989) J Biol Chem 264:5503–5509.) PGEX vectors (APB) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol 153:516–544.)

In cases where plant expression vectors are used, the expression of sequences encoding HHLM may be driven by any of a number of promoters. For example, viral promoters such as the 35S and 19S promoters of CaMV may be used alone or in combination with the omega leader sequence from TMV (Takamatsu (1987) EMBO J 6:307–311). Alternatively, plant promoters such as the small subunit of RUBISCO or heat shock promoters may be used. (See, e.g., Coruzzi et al. (1984) EMBO J 3:1671–1680; Broglie et al. (1984) Science 224:838–843; and Winter et al. (1991) Results Probl Cell Differ 17:85–105.) These constructs can be introduced into plant cells by direct DNA transformation or pathogen-mediated transfection. Such techniques are described in a number of generally available reviews. (See, *McGraw Hill Yearbook of Science and Technology* (1992) McGraw Hill, New York N.Y.; pp. 191–196.) An insect system may also be used to express HHLM. For example, in one such system, *Autographa californica* nuclear polyhedrosis virus (AcNPV) is used as a vector to express foreign genes in *Spodoptera frugiperda* cells or in *Trichoplusia* larvae. The sequences encoding HHLM may be cloned into a non-essential region of the virus, such as the polyhedrin gene, and placed under control of the polyhedrin promoter. Successful insertion of sequences encoding HHLM will render the polyhedrin gene inactive and produce recombinant virus lacking coat protein. The recombinant viruses may then be used to infect, for example, *S. frugiperda* cells or *Trichoplusia* larvae in which HHLM may be expressed. (See, e.g., Engelhard et al. (1994) Proc Natl Acad Sci 91:3224–3227.)

In mammalian host cells, a number of viral-based expression systems may be utilized. In cases where an adenovirus is used as an expression vector, sequences encoding HHLM may be ligated into an adenovirus transcription/translation complex consisting of the late promoter and tripartite leader sequence. Insertion in a non-essential E1 or E3 region of the viral genome may be used to obtain a viable virus which is capable of expressing HHLM in infected host cells. (See, e.g., Logan and Shenk (1984) Proc Natl Acad Sci 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HHLM. Such signals include the ATG initiation codon and adjacent sequences. In cases where sequences encoding HHLM and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf et al. (1994) Results Probl Cell Differ 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Manssas Va.) and may be chosen to ensure the correct modification and processing of the foreign protein.

For long term, high yield production of recombinant proteins, stable expression is preferred. For example, cell lines capable of stably expressing HHLM can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk- or apr cells, respectively. (See, e.g., Wigler et al. (1977) Cell 11:223–232; and Lowy et al. (1980) Cell 22:817–823.) Also, antimetabolite, antibiotic, or herbicide resistance can be used as the basis for selection. For example, dhfr confers resistance to methotrexate; npt confers resistance to the aminoglycosides neomycin and G418; and als or pat confer resistance to chlorsulfuron and phosphinotricin acetyltransferase, respectively. (See, e.g., Wigler et al. (1980) Proc Natl Acad Sci 77:3567–3570; and Colbere-Garapin et al. (1981) J Mol Biol 150:1–14) Additional selectable genes have been described, e.g., trpB, which allows cells to utilize indole in place of tryptophan, or hisD, which allows cells to utilize histinol in place of histidine. (See, e.g., Hartman and Mulligan (1988) Proc Natl Acad Sci 85:8047–8051.) Visible markers, e.g., anthocyanins, β glucuronidase and its substrate GUS, luciferase and its substrate luciferin may be used. Green fluorescent proteins (GFP; Clontech, Palo Alto Calif.) can also be used. These markers can be used not only to identify transformants, but also to quantify the amount of transient or stable protein expression attributable to a specific vector system. (See, e.g., Rhodes et al. (1995) Methods Mol Biol 55:121–131.)

Although the presence/absence of marker gene expression suggests that the gene of interest is also present, the presence and expression of the gene may need to be confirmed. For example, if the sequence encoding HHLM is inserted within a marker gene sequence, transformed cells containing sequences encoding HHLM can be identified by the absence of marker gene function. Alternatively, a marker gene can be placed in tandem with a sequence encoding HHLM under the control of a single promoter. Expression of the marker gene in response to induction or selection usually indicates expression of the tandem gene as well.

Alternatively, host cells which contain the nucleic acid sequence encoding HHLM and express HHLM may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HHLM can be detected by DNA-DNA or DNA-RNA hybridization or amplification using probes or fragments or fragments of polynucleotides encoding HHLM. Nucleic acid amplification based assays involve the use of oligonucleotides or oligomers based on the sequences encoding HHLM to detect transformants containing DNA or RNA encoding HHLM.

A variety of protocols for detecting and measuring the expression of HHLM, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HHLM is preferred, but a competitive binding assay may be employed. These and other assays are well described in the art. (See, e.g., Hampton et al. (1990) *Serological Methods, a Laboratory Manual*, APS Press, St Paul Min., Section IV; and Maddox et al. (1983)J Exp Med 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HHLM include oligolabeling, nick translation, end-labeling, or PCR amplification using a labeled nucleotide. Alternatively, the sequences encoding HHLM, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by APB and Promega (Madison Wis.). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HHLM may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HHLM may be designed to contain signal sequences which direct secretion of HHLM through a prokaryotic or eukaryotic cell membrane. Other constructions may be used to join sequences encoding HHLM to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system. (Immunex, Seattle Wash.). The inclusion of cleavable linker sequences, such as those specific for Factor XA or enterokinase (Invitrogen, San Diego Calif.), between the purification domain and the HHLM-encoding sequence may be used to facilitate purification. One such expression vector provides for expression of a fusion protein containing HHLM and a nucleic acid encoding 6 histidine residues preceding a thioredoxin or an enterokinase cleavage site. The histidine residues facilitate purification on immobilized metal ion affinity chromatography. (See, e.g., Porath et al. (1992) Prot Exp Purif 3:263–281.) The enterokinase cleavage site provides a means for purifying HHLM from the fusion protein. (See, e.g., Kroll et al. (1993) DNA Cell Biol 12:441–453.)

Fragments of HHLM may be produced not only by recombinant production, but also by direct peptide synthesis using solid-phase techniques. (See, e.g., Creighton (1984) Protein: Structures and Molecular Properties, pp. 55–60, W.H. Freeman, New York N.Y.) Protein synthesis may be performed by manual techniques or by automation. Automated synthesis may be achieved, for example, using the ABI 431A peptide synthesizer (PE Biosystems). Various fragments of HHLM may be synthesized separately and then combined to produce the full length molecule.

THERAPEUTICS

Chemical and structural homology exists among the human hydrolase-like molecules of the invention. In addition, HHLM is expressed in cancerous or immortalized tissues and tissues associated with inflammation and the autoimmune response. There fore, HHLM appears to play a role in cell proliferation disorders, and autoimmune disorders.

Therefore, in one embodiment, an antagonist of HHLM may be administered to a subject to treat or prevent a cell proliferation disorder. Such a disorder may include, but is not limited to, arteriosclerosis, atherosclerosis, bursitis, cirrhosis, hepatitis, mixed connective tissue disease, myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, nerves, ovary, pancreas, parathyroid, penis, prostate, salivary glands, skin, spleen, testis, thymus, thyroid, and uterus. In one aspect, an antibody which specifically binds HHLM may be used directly as an antagonist or indirectly as a targeting or delivery mechanism for bringing a pharmaceutical agent to cells or tissue which express HHLM.

In an additional embodiment, a vector expressing the complement of the polynucleotide encoding HHLM may be administered to a subject to treat or prevent a cell proliferation disorder including, but not limited to, those described above.

In a further embodiment, an antagonist of HHLM may be administered to a subject to treat or prevent an autoimmune disorder. Such a disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scieroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

In an additional embodiment, a vector expressing the complement of the polynucleotide encoding HHLM may be administered to a subject to treat or prevent an autoimmune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HHLM may be produced using methods which are generally known in the art. In particular, purified HHLM may be used to produce antibodies or to screen libraries of pharmaceutical agents to identify those which specifically bind HHLM. Antibodies to HHLM may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HHLM or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium paryum* are especially preferable.

It is preferred that the oligopeptides, peptides, or fragments used to induce antibodies to HHLM have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HHLM amino acids may be fused with those of another protein, such as KLH, and antibodies to the chimeric molecule may be produced.

Monoclonal antibodies to HHLM may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor etal. (1985) J Immunol Methods 81:31–42; Cote et al. (1983) Proc Natl Acad Sci 80:2026–2030; and Cole et al. (1984) Mol Cell Biol 62:109–120.) In addition, techniques developed for the production of "chimeric antibodies," such as the splicing of mouse antibody genes to human antibody genes to obtain a molecule with appropriate antigen specificity and biological activity, can be used. (See, e.g., Morrison et al. (1984) Proc Natl Acad Sci 81:6851–6855; Neuberger et al. (1984) Nature 312:604–608; and Takeda et al. (1985) Nature 314:452–454.) Alternatively, techniques described for the production of single chain antibodies may be adapted, using methods known in the art, to produce HHLM-specific single chain antibodies. Antibodies with related specificity, but of distinct idiotypic composition, may be generated by chain shuffling from random combinatorial immunoglobulin libraries. (See, e.g., Burton (1991) Proc Natl Acad Sci 88:10134–10137.)

Antibodies may also be produced by inducing in vivo production in the lymphocyte population or by screening immunoglobulin libraries or panels of highly specific binding reagents as disclosed in the literature. (See, e.g., Orlandi et al. (1989) Proc Natl Acad Sci 86: 3833–3837; Winter et al. (1991) Nature 349:293–299.)

Antibody fragments which contain specific binding sites for HHLM may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HHLM and its specific antibody. A two-site, monoclonal-based immunoassay utilizing monoclonal antibodies reactive to two non-interfering HHLM epitopes is preferred, but a competitive binding assay may also be employed. (Maddox, supra.)

In another embodiment of the invention, the polynucleotides encoding HHLM, or any fragment or complement thereof, may be used for therapeutic purposes. In one aspect, the complement of the polynucleotide encoding HHLM may be used in situations in which it would be desirable to block the transcription of the mRNA. In particular, cells may be transformed with sequences complementary to polynucleotides encoding HHLM. Thus, complementary molecules or fragments may be used to modulate HHLM activity, or to achieve regulation of gene function. Such technology is now well known in the art, and sense or antisense oligonucleotides or larger fragments can be designed from various locations along the coding or control regions of sequences encoding HHLM.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HHLM. (See, e.g., Sambrook, supra; and Ausubel, supra.)

Genes encoding HHLM can be turned off by transforming a cell or tissue with expression vectors which express high levels of a polynucleotide, or fragment thereof, encoding HHLM. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HHLM. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. (1994) in Huber and Carr, *Molecular and Immunologic Approaches*, Futura Publishing Co., Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HHLM.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HHLM. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues. RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman et al. (1997) Nat Biotech 15:462466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HHLM, antibodies to HHLM, and mimetics, agonists, antagonists, or inhibitors of HHLM. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HHLM, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HHLM or fragments thereof, antibodies of HHLM, and agonists, antagonists or inhibitors of HHLM, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HHLM may be used for the diagnosis of disorders characterized by expression of HHLM, or in assays to monitor patients being treated with HHLM or agonists, antagonists, or inhibitors of HHLM. Antibodies useful for diagnostic purposes may be prepared in the same manner as described above for therapeutics. Diagnostic assays for HHLM include methods which utilize the antibody and a label to detect HHLM in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HHLM, including ELISAs, RIAs, and FACS, are known in the art and provide a basis for diagnosing altered or abnormal levels of HHLM expression. Normal or standard values for HHLM expression are established by combining body fluids or cell extracts taken from normal mammalian subjects, preferably human, with antibody to HHLM under conditions suitable for complex formation The amount of standard complex formation may be quantitated by various methods, preferably by photometric means. Quantities of HHLM expressed in subject, control, and disease samples from biopsied tissues are compared with the standard values. Deviation between standard and subject values establishes the parameters for diagnosing disease.

In another embodiment of the invention, the polynucleotides encoding HHLM may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HHLM may be correlated with disease. The diagnostic assay may be used to determine absence, presence, and excess expression of HHLM, and to monitor regulation of HHLM levels during therapeutic intervention.

In one aspect, hybridization with PCR probes which are capable of detecting polynucleotide sequences, including genomic sequences, encoding HHLM or closely related molecules may be used to identify nucleic acid sequences which encode HHLM. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HHLM, alleles, or related sequences.

Probes may also be used for the detection of related sequences, and should preferably have at least 50% sequence identity to any of the HHLM-encoding sequences. The hybridization probes of the subject invention may be DNA or RNA and may be derived from the sequence SEQ ID NOs:9–16 and 17–55, or from genomic sequences including promoters, enhancers, and introns of the HHLM gene.

Means for producing specific hybridization probes for DNAs encoding HHLM include the cloning of polynucleotide sequences encoding HHLM or HHLM derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HHLM may be used for the diagnosis of a disorder associated with expression of HHLM. Examples of such a disorder include, but are not limited to, cell proliferation disorders such as arteriosclerosis, atherosclerosis, bursitis, cirrhosis, hepatitis, mixed connective tissue disease, myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, nerves, ovary, pancreas, parathyroid, penis, prostate, salivary glands, skin, spleen, testis, thymus, thyroid, and uterus; and autoimmune disorders such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding HHLM may be used in Southern or northern analysis, dot blot, or other membrane-based technologies; in PCR technologies; in dipstick, pin, and multiwell assays; and in microarrays utilizing fluids or tissues from patients to detect altered HHLM expression. Such qualitative or quantitative methods are well known in the art.

In a particular aspect, the nucleotide sequences encoding HHLM may be useful in assays that detect the presence of associated disorders, particularly those mentioned above. The nucleotide sequences encoding HHLM may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HHLM in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HHLM, a normal or standard profile for expression is established. This may be accomplished by combining body fluids or cell extracts taken from normal subjects, either animal or human, with a sequence, or a fragment thereof, encoding HHLM, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

Additional diagnostic uses for oligonucleotides designed from the sequences encoding HHLM may involve the use of PCR. These oligomers may be chemically synthesized, generated enzymatically, or produced in vitro. Oligomers will preferably contain a fragment of a polynucleotide encoding HHLM, or a fragment of a polynucleotide complementary to the polynucleotide encoding HHLM, and will be employed under optimized conditions for identification of a specific gene or condition. Oligomers may also be employed under less stringent conditions for detection or quantitation of closely related DNA or RNA sequences.

Methods which may also be used to quantitate the expression of HHLM include radiolabeling or biotinylating nucleotides, coamplification of a control nucleic acid, and interpolating results from standard curves. (See, e.g., Melby et al. (1993) J Immunol Methods 159:235–244; and Duplaa et al. (1993) Anal Biochem 212:229–236.) The speed of quantitation of multiple samples may be accelerated by running the assay in a multiwell format where the oligomer of interest is presented in various dilutions and a spectrophotometric or colorimetric response gives rapid quantitation.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir et al. (1999) Mol Carcinog 24:153–159; Steiner and Anderson (2000) Toxicol Lett 112–113:467471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00-02 from the National Institute of Environmental Health Sciences, released Feb. 29, 2000, available at http:I/www.niehs.nih.gov/oc/news/toxchip.htm.) Therefore, it is important and desirable in toxicological screening using toxicant signatures to include all expressed gene sequences.

Another particular embodiment relates to the use of the polypeptide sequences of the present invention to analyze a protein expression image of a tissue or cell type. A protein expression image represents the global pattern of expression at the protein level. Patterns of expression at the protein level are analyzed by quantifying the number of expressed proteins and their relative abundance under given conditions and at a given time. Thus a protein expression image may be generated by separating and analyzing the polypeptides of a particular tissue or cell type. In one embodiment, the separation is performed using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized, typically by staining with an agent, including but not limited to Coomassie Blue, silver, or fluorescent stains. The optical densities of the protein spots are proportional to the levels of those proteins in the sample, and the proteins in the spots are sequenced using standard methods. The optical densities of protein spots from treated and untreated samples are compared to identify any changes related to the treatment. Protein spots are identified by comparing partial sequences from the spots, preferably of at least 5 contiguous amino acid residues, to the polypeptide sequences of the present invention. In some cases, identification is uncertain with a partial sequence of 5 amino acid residues, and further sequence information is collected for definitive identification.

A protein expression image may also be generated using antibodies specific for HHLM to quantify the levels of expression at the protein level. In one embodiment, the antibodies are used as elements on a microarray, and protein expression levels are quantified by exposing the microarray to the sample and detecting the levels of protein bound to each array element (Lueking et al. (1999) Anal Biochem 270:103–111; Mendoze et al. (1999) Biotechniques 27:778–788). Detection may be performed by a variety of methods known in the art, for example by reacting the proteins in the sample with a thiol- or amino-reactive fluorescent compound and detecting the amount of fluorescence bound at each array element.

Toxicant signatures at the protein level are also useful for toxicological screening, and should be analyzed in parallel with toxicant signatures at the transcript level. There is a poor correlation between transcript and protein abundances for some proteins in some tissues (Anderson and Seilheimer (1997) Electrophoresis 18:533–537), so protein level toxicant signatures may be useful in the analysis of compounds which do not significantly affect the transcript image. In addition, the analysis of transcripts in body fluids is difficult, due to rapid degradation of mRNA, so the protein expression image may be more reliable and informative in such cases.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

In another embodiment, the toxicity of a test compound is assessed by treating a biological sample containing proteins with the test compound. Proteins that are expressed in the treated biological sample are separated so that the amount of each protein can be quantified. The amounts of the proteins are compared to the amounts of corresponding proteins in an untreated biological sample. Differences in the amounts of proteins between the two samples are indicative of a toxic response to the test compound in the treated sample. Individual proteins from the separated proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies, so that the amounts of the proteins recognized by the antibodies may be quantified. The amounts of the proteins in the treated biological sample are compared with the amounts in an untreated biological sample. Differences in the amounts of proteins between the two samples are indicative of a toxic response to the test compound in the treated sample.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Chee et al. (1995) PCT application WO95/11995; Fodor et al. (1995) U.S. Pat. No. 5,424,186; Brennan et al. (1995) U.S. Pat. No. 5,474,796; Schena et al. (1996) Proc Natl Acad Sci 93:10614–10619; Baldeschweiler et al. (1995) PCT application WO95/251116; Shalon et al. (1995) PCT application WO95/35505; Lockhart et al. (1996) Nat Biotech 14:1675–1680; Heller et al. (1997) Proc Natl Acad Sci 94:2150–2155; and Heller et al. (1997) U.S. Pat. No. 5,605,662.)

In another embodiment of the invention, nucleic acid sequences encoding HHLM may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price (1993) Blood Rev 7:127–134; and Trask (1991) Trends Genet 7:149–154.)

Fluorescent in situ hybridization (FISH) may be correlated with other physical chromosome mapping techniques and genetic map data. (See, e.g., Heinz-Ulrich, etal. (1995) in Meyers (ed.) *Molecular Biology and Biotechnology*, VCH Publishers New York N.Y., pp. 965–968.) Examples of genetic map data can be found in various scientific journals or at the Online Mendelian Inheritance in Man (OMIM) site. Correlation between the location of the gene encoding HHLM on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HHLM, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HHLM and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HHLM, or fragments thereof, and washed. Bound HHLM is then detected by methods well known in the art. Purified HHLM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HHLM specifically compete with a test compound for binding HHLM. In this manner, antibodies can be used to detect the presence of any peptide which shares one or more antigenic determinants with HHLM.

In additional embodiments, the nucleotide sequences which encode HHLM may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

For purposes of example, the preparation and sequencing of the LUNGNOT10 cDNA library, from which Incyte Clone 1376382 was isolated, is described. Preparation and sequencing of cDNAs in libraries in the LIFESEQ database (Incyte Genomics, Inc., Palo Alto Calif.) have varied over time, and the gradual changes involved use of kits, plasmids, and machinery available at the particular time the library was made and analyzed.

I LUNGNOT10 cDNA Library Construction

The LUNGNOT10 cDNA library was constructed from normal lung tissue obtained from a 23-week-old Caucasian male fetus. The frozen tissue was homogenized and lysed using a POLYTRON homogenizer (PT-3000; Brinkmann Instruments, Westbury N.J.) in guanidinium isothiocyanate solution.

The lysate was centrifuged over a 5.7 M CsCl cushion using an SW28 rotor in an L8–70M ultracentrifuge (Beckman Coulter, Fullerton Calif.) for 18 hours at 25,000 rpm at ambient temperature. The RNA was extracted with acid phenol, pH 4.0, precipitated using 0.3 M sodium acetate and 2.5 volumes of ethanol, resuspended in RNAse-free water, and treated with DNase at 37° C. RNA extraction and precipitation were repeated as before. The mRNA was isolated with the OLIGOTEX kit (Qiagen, Chatsworth Calif.) and used to construct the cDNA library.

The mRNA was handled according to the recommended protocols in the SUPERSCRIPT plasmid system(Life Technologies). cDNAs were fractionated on a SEPHAROSE CL4B column (APB), and those cDNAs exceeding 400 bp were ligated into pINCY I plasmid (Incyte Genomics). The plasmid pINCY was subsequently transformed into DH5a competent cells (Life Technologies).

II Isolation and Sequencing of cDNA Clones

Plasmid DNA was released from the cells and purified using the REAL PREP 96 plasmid kit (Qiagen). This kit enabled the simultaneous purification of 96 samples in a 96-well block using multi-channel reagent dispensers. The recommended protocol was employed except for the following changes:1) the bacteria were cultured in 1 ml of sterile Terrific Broth (Life Technologies) with carbenicillin (Carb) at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using a MICROLAB 2200 system (Hamilton) in combination with DNA ENGINE thermal cyclers (MJ Research) and sequenced by the method of Sanger and Coulson (1975; J Mol Biol 94:441–448) using ABI PRISM 373 or 377 sequencing systems (PE Biosystems); and the reading frame was determined.

III. Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST 2 (Altschul et al. supra; Altschul, supra) to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992; Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-4}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the electronic stringency for an exact match was set at 70, and the conservative lower limit for an exact match was set at approximately 40 (with 1–2% error due to uncalled bases).

The BLAST software suite, freely available sequence comparison algorithms (NCBI, Bethesda MD; http://www.ncbi.nlm.nih.gov/gorf/bl2.html), includes various sequence analysis programs including "blastn" that is used to align nucleic acid molecules and BLAST 2 that is used for direct pairwise comparison of either nucleic or amino acid molecules. BLAST programs are commonly used with gap and other parameters set to default settings, e.g.: Matrix: BLOSUM62; Reward for match: 1; Penalty for mismatch: −2; Open Gap: 5 and Extension Gap: 2 penalties; Gap×drop-off: 50; Expect: 10; Word Size: 11; and Filter: on. Identity is measured over the entire length of a sequence or some smaller portion thereof. Brenner et al. (1998; Proc Natl Acad Sci 95:6073–6078, incorporated herein by reference) analyzed the BLAST for its ability to identify structural homologs by sequence identity and found 30% identity is a reliable threshold for sequence alignments of at least 150 residues and 40%, for alignments of at least 70 residues.

The cDNA was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel et al. supra, ch. 4 and 16.)

Analogous computer techniques applying BLAST are used to search for identical or related molecules in nucleotide databases such as GenBank or LIFESEQ database (Incyte Genomics). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximumBLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HHLM occurs. Abundance and percent abundance are also reported. Abundance directly reflects the number of times a particular transcript is represented in a cDNA library, and percent abundance is abundance divided by the total number of sequences examined in the cDNA library.

V. Extension of HHLM Encoding Polynucleotides

The nucleic acid sequences of Incyte Clones 094168, 195647, 507537, 971204, 1376382, 2011230, 2768301, and 2886583 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 primer analysis software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (PE Biosystems) and thoroughly mixing the enzyme and reaction mix. PCR was performed using the DNA ENGINE thermal cycler (M.J. Research), beginning with 40 pmol of each primer and the recommended concentrations of all other components of the kit, with the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to.determine which reactions were successful in extending the sequence. Bands thought to contain the largest products were excised from the gel, purified using QIAQUICK kit (Qiagen), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2×Carb. The following day, several colonies were randomly picked from each plate and cultured in 150 μl of liquid LB/2×Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NOs:916 and 17–55 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NOs:9–16 and 17–55 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 primer analysis software (National Biosciences) and labeled by combining 50 pmol of each oligomer, 250 μCi of [γ-$^{32}$P] adenosine triphosphate (APB), and T4 polynucleotide kinase (NEN Life Science Products, Boston Mass.). The labeled oligonucleotides are substantially purified using a SEPHADEX G-25 superfine resin column (APB). An aliquot containing $10^7$ counts per minute of the labeled probe is used in a typical membrane-based hybridization analysis of human genomic DNA digested with one of the following endonucleases: Ase I, Bg111, Eco R1, Pst I, Xba 1, or Pvu II (NEN Life Science Products).

The DNA from each digest is fractionated on a 0.7 percent agarose gel and transferred to NYTRAN PLUS membranes (Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Eastman Kodak, Rochester N.Y.) is exposed to the blots for several hours, hybridization patterns are compared visually.

VII. Microarrays

To produce oligonucleotides for a microarray, one of the nucleotide sequences of the present invention is examined using a computer algorithm which starts at the 3' end of the nucleotide sequence. For each, the algorithm identifies oligomers of defined length that are unique to the nucleic acid sequence, have a GC content within a range suitable for hybridization, and lack secondary structure that would interfere with hybridization. The algorithm identifies approximately 20 oligonucleotides corresponding to each nucleic acid sequence. For each sequence-specific oligonucleotide, a pair of oligonucleotides is synthesized in which the first oligonucleotides differs from the second oligonucleotide by one nucleotide in the center of the sequence. The oligonucleotide pairs can be arranged on a substrate, e.g. a silicon chip, using a light-directed chemical process. (See, e.g., Chee, supra.)

Probe sequences may be selected by screening a large number of clones from a variety of cDNA libraries in order to find sequences with conserved protein motifs common to genes coding for signal sequence containing polypeptides. In one embodiment, sequences identified from cDNA libraries, are analyzed to identify those gene sequences with conserved protein motifs using an appropriate analysis program, e.g., the Block 2 bioanalysis program (Incyte Genomics). This motif analysis program, based on sequence information contained in the Swiss-Prot Database and PROSITE, is a method of determining the function of uncharacterized proteins translated from genomic or cDNA sequences. (See, e.g., Bairoch et al. (1997) Nucleic Acids Res 25:217–221; and Attwood et al. (1997) J Chem Inf Comput Sci 37:417–424.) PROSITE may be used to identify functional or structural domains that cannot be detected using conserved motifs due to extreme sequence divergence. The method is based on weight matrices. Motifs identified by this method are then calibrated against the SWISS-PROT database in order to obtain a measure of the chance distribution of the matches.

In another embodiment, Hidden Markov models (HMMs) may be used to find shared motifs, specifically consensus sequences. (See, e.g., Pearson and Lipman (1988) Proc Natl Acad Sci 85:2444–2448; and Smith and Waterman (1981) J Mol Biol 147:195–197.) HMMs were initially developed to examine speech recognition patterns, but are now being used in a biological context to analyze protein and nucleic acid sequences as well as to model protein structure. (See, e.g., Krogh et al. (1994) J Mol Biol 235:1501–1531; and Collin et al. (1993) Protein Sci 2:305–314.) HMMs have a formal probabilistic basis and use position-specific scores for amino acids or nucleotides. The algorithm continues to incorporate information from newly identified sequences to increase its motif analysis capabilities.

In the alternative, a chemical coupling procedure and an ink jet device can be used to synthesize oligomers on the surface of a substrate. (See, e.g., Baldeschweiler, supra.) An array analogous to a dot or slot blot may also be used to arrange and link fragments or oligonucleotides to the surface of a substrate using or thermal, UV, mechanical, or chemical bonding procedures, or a vacuum system. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each oligonucleotide sequence on the microarray may be assessed through analysis of the scanned images.

In another alternative, full-length cDNAs or Expressed Sequence Tags (ESTs) comprise the elements of the microarray. Full-length cDNAs or ESTs corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed, by thermal and chemical and subsequent drying. (See, e.g., Schena et al. (1995) Science 270:467–470; and Shalon et al. (1996) Genome Res 6:639–645.) Fluorescent probes are prepared and used for hybridization to the elements on the substrate. The substrate is analyzed by procedures described above.

VIII. Complementary Polynucleotides

Sequences complementary to the HHLM-encoding sequences, or any parts thereof, are used to detect, decrease, or inhibit expression of naturally occurring HHLM. Although use of oligonucleotides comprising from about 15 to 30 base pairs is described, essentially the same procedure is used with smaller or with larger sequence fragments. Appropriate oligonucleotides are designed using OLIGO 4.06 primer analysis software (National Biosciences) and the coding sequence of HHLM. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HHLM-encoding transcript.

IX. Expression of HHLM

Expression of HHLM is accomplished by subcloning the cDNA into an appropriate vector and transforming the vector into host cells. This vector contains an appropriate promoter, e.g., β-galactosidase upstream of the cloning site, operably associated with the cDNA of interest. (See, e.g., Sambrook, supra, pp. 404433; and Rosenberg et al. (1983) Methods Enzymol 101:123–138.) Induction of an isolated, transformed bacterial strain with isopropyl beta-D-thiogalactopyranoside using standard methods produces a fusion protein which consists of the first 8 residues of β-galactosidase, about 5 to 15 residues of linker, and the full length protein. The signal residues direct the secretion of HHLM into bacterial growth media which can be used directly in the following assay for activity.

X. Demonstration of HHLM Activity

For purposes of example, an assay measuring the phosphatase activity of an HHLM molecule is described. Varying amounts of HHLM are incubated with a fixed amount of [$^{32}$P]-labeled myelin basic protein (MBP). After incubation under appropriate conditions of time, temperature, pH, and ionic strength described by Li et al. (1995, Biochemistry 34:1988–1996), the proteins are precipitated with cold trichloroacetic acid and collected on nitrocellulose filters with a 0.45 μm pore size (Millipore, Bedford Mass.). The filters are dried and immersed in a commercially available scintillation fluid prior to counting in a scintillation counter (Beckman Coulter). The amount of [$^{32}$P]phosphate released from MBP by HHLM is proportional to the activity of HHLM in the sample.

XI. Production of HHLM Specific Antibodies

HHLM substantially purified using PAGE electrophoresis (see, e.g., Harrington (1990) Methods Enzymol 182:488495), or other purification techniques, is used to immunize rabbits and to produce antibodies using standard protocols. The HHLM amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an ABI 431A peptide synthesizer (PE Biosystems) using Fmoc-chemistry and coupled to KLH (Sigma Aldrich, St. Louis Mo.) by reaction with N-maleimidobenzoyl-N-hydroxysuccinimide ester to increase immunogenicity. (See, e.g., Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HHLM Using Specific Antibodies

Naturally occurring or recombinant HHLM is substantially purified by immunoaffinity chromatography using antibodies specific for HHLM. An immunoaffinity column is constructed by covalently coupling anti-HHLM antibody to an activated chromatographic resin, such as CNBr-activated SEPHAROSE (APB). After the coupling, the resin is blocked and washed according to the manufacturer's instructions.

Media containing HHLM are passed over the immunoaffinity column, and the column is washed conditions that allow the preferential absorbance of HHLM (e.g., high ionic strength buffers in the presence of detergent). The column is eluted under conditions that disrupt antibody/HHLM binding (e.g., a buffer of pH 2 to pH 3, or a high concentration of a chaotrope, such as urea or thiocyanate ion), and HHLM is collected.

XIII. Identification of Molecules Which Interact with HHLM

HHLM, or biologically active fragments thereof, are labeled with $^{125}$I Bolton-Hunter reagent. (See, e.g., Bolton et al. (1 973) Biochem J 133:529–539.) Candidate molecules previously arrayed in the wells of a multi-well plate are incubated with the labeled HHLM, washed, and any wells with labeled HHLM complex are assayed. Data obtained using different concentrations of HHLM are used to calculate values for the number, affinity, and association of HHLM with the candidate molecules. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polypeptide comprising an amino acid sequence, wherein said polypeptide is selected from the group consisting of:
   a) a polypeptide comprising the amino acid sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8,
   b) a naturally occurring polypeptide comprising an amino acid sequence at least 81% identical to the full length of an amino acid sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8 and which has hydrolase activity,
   c) a biologically active fragment of a polypeptide having the amino acid sequence of SEQ ID NO:1, SEQ ID NO:2, SEQ ID NO:3, SEQ ID NO:4, SEQ ID NO:6, SEQ ID NO:7 or SEQ ID NO:8 and which has hydrolase activity, and
   d) an immunogenic fragment comprising at least 15 contiguous amino acid residues of SEQ ID NO:1, SEQ ID NO:2, SEQ ID NO:3, SEQ ID NO:4, SEQ ID NO:6, SEQ ID NO:7 or SEQ ID NO:8, wherein said immunogenic fragment generates an antibody that specifically binds to the polypeptide having the amino acid sequence of SEQ ID NO:1, SEQ ID NO:2, SEQ ID NO:3, SEQ ID NO:4, SEQ ID NO:6, SEQ ID NO:7 or SEQ ID NO:8.

2. An isolated polypeptide of claim 1, comprising the sequence of SEQ ID NO:1.

3. An isolated polypeptide of claim 1, comprising the sequence of SEQ ID NO:2.

4. An isolated polypeptide of claim 1, comprising the sequence of SEQ ID NO:3.

5. An isolated polypeptide of claim 1, comprising the sequence of SEQ ID NO:4.

6. An isolated polypeptide of claim 1, comprising the sequence of SEQ ID NO:5.

7. An isolated polypeptide of claim 1, comprising the sequence of SEQ ID NO:6.

8. An isolated polypeptide of claim 1, comprising the sequence of SEQ ID NO:7.

9. An isolated polypeptide of claim 1, comprising the sequence of SEQ ID NO:8.

10. A composition comprising a polypeptide of claim 1 and an acceptable excipient.

11. A method for screening a compound for effectiveness as an agonist of a polypeptide of claim 1, the method comprising:
   a) exposing a sample comprising a polypeptide of claim 1 to a compound, and
   b) detecting agonist activity in the sample.

12. A method for screening a compound for effectiveness as an antagonist of a polypeptide of claim 9 the method comprising:
   a) exposing a sample comprising a polypeptide of claim 1 to a compound, and
   b) detecting antagonist activity in the sample.

13. A method of screening for a compound that specifically binds to the polypeptide of claim 1, the method comprising:
   a) combining the polypeptide of claim 1 with at least one test compound under suitable conditions, and
   b) detecting binding of the polypeptide of claim 1 to the test compound, thereby identifying a compound that specifically binds to the polypeptide of claim 1.

14. A method of screening for a compound that modulates the activity of the polypeptide of claim 1, said method comprising:
   a) combining the polypeptide of claim 1 with at least one test compound under conditions permissive for the activity of the polypeptide of claim 1,
   b) assessing the activity of the polypeptide of claim 1 in the presence of the test compound, and
   c) comparing the activity of the polypeptide of claim 1 in the presence of the test compound with the activity of the polypeptide of claim 9 in the absence of the test compound, wherein a change in the activity of the polypeptide of claim 1 in the presence of the test compound is indicative of a compound that modulates the activity of the polypeptide of claim 9.

* * * * *

UNITED STATES PATENT AND TRADEMARK OFFICE
CERTIFICATE OF CORRECTION

PATENT NO. : 6,518,029 B1
DATED : February 11, 2003
INVENTOR(S) : Bandman et al.

It is certified that error appears in the above-identified patent and that said Letters Patent is hereby corrected as shown below:

<u>Column 102,</u>
Lines 19 and 23, please replace "claim 9" with -- claim 1 --.

Signed and Sealed this

Twelfth Day of August, 2003

JAMES E. ROGAN
*Director of the United States Patent and Trademark Office*